US011773076B2

(12) United States Patent
Zhao et al.

(10) Patent No.: US 11,773,076 B2
(45) Date of Patent: Oct. 3, 2023

(54) CRYSTALLINE FORMS OF A SOMATOSTATIN MODULATOR

(71) Applicant: Crinetics Pharmaceuticals, Inc., San Diego, CA (US)

(72) Inventors: Yuxin Zhao, San Diego, CA (US); Jayachandra P. Reddy, San Diego, CA (US); Lauren Maceachern, Halifax (CA); Samer Kahwaji, Halifax (CA); Evans Monyoncho, San Diego, CA (US); Peter Mueller, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 32 days.

(21) Appl. No.: 17/673,579

(22) Filed: Feb. 16, 2022

(65) Prior Publication Data

US 2022/0259175 A1 Aug. 18, 2022

Related U.S. Application Data

(60) Provisional application No. 63/150,262, filed on Feb. 17, 2021.

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; C07B 2200/13
See application file for complete search history.

(56) References Cited

U.S. PATENT DOCUMENTS

| | | | |
|---|---|---|---|
| 6,025,372 A | 2/2000 | Yang et al. | |
| 6,127,343 A | 10/2000 | Ankersen et al. | |
| 7,754,744 B2 | 7/2010 | Binggeli et al. | |
| 8,110,574 B2 | 2/2012 | Thurieau et al. | |
| 8,778,925 B2 | 7/2014 | McDonald et al. | |
| 9,630,976 B2 | 4/2017 | Ishida et al. | |
| 9,643,951 B2 | 5/2017 | Ishida et al. | |
| 10,214,540 B2 | 2/2019 | Ishida et al. | |
| 10,696,689 B2 | 6/2020 | Han et al. | |
| 11,072,598 B2 | 7/2021 | Han et al. | |
| 11,186,590 B2 | 11/2021 | Han et al. | |
| 11,479,540 B2 * | 10/2022 | Zhao ........................ | A61P 3/10 |
| 2006/0281764 A1 | 12/2006 | Gaul et al. | |
| 2011/0059971 A1 | 3/2011 | Thurieau et al. | |
| 2013/0040978 A1 | 2/2013 | Duffy et al. | |
| 2015/0232478 A1 | 8/2015 | Ishida et al. | |
| 2016/0311794 A1 | 10/2016 | Ishida et al. | |
| 2020/0000816 A1 | 1/2020 | Ishida et al. | |
| 2021/0040087 A1 | 2/2021 | Zhao et al. | |
| 2021/0047287 A1 | 2/2021 | Zhao et al. | |
| 2022/0048924 A1 | 2/2022 | Han et al. | |
| 2022/0144802 A1 | 5/2022 | Zhao et al. | |

FOREIGN PATENT DOCUMENTS

| | | |
|---|---|---|
| CA | 2925651 A1 | 4/2015 |
| CN | 105593221 A | 5/2016 |
| CN | 110300749 A | 10/2019 |
| EP | 2871179 A1 | 5/2015 |
| EP | 3053916 A1 | 8/2016 |
| EP | 3053961 A1 | 8/2016 |
| EP | 3053916 B1 | 1/2019 |
| EP | 3581569 A1 | 12/2019 |
| JP | 2008543760 A | 12/2008 |
| WO | WO-2008051272 A2 | 5/2008 |
| WO | WO-2009051705 A1 | 4/2009 |
| WO | WO-2009158467 A2 | 12/2009 |
| WO | WO-2010041054 A1 | 4/2010 |
| WO | WO-2011027249 A2 | 3/2011 |
| WO | WO-2011144891 A1 | 11/2011 |
| WO | WO-2014007228 A1 | 1/2014 |
| WO | WO-2015046482 A1 | 4/2015 |
| WO | WO-2018013676 A1 | 1/2018 |
| WO | WO-2018147300 A1 | 8/2018 |
| WO | WO-2018170284 A1 | 9/2018 |
| WO | WO-2019023278 A1 | 1/2019 |
| WO | WO-2019157458 A1 | 8/2019 |
| WO | WO-2020061046 A1 | 3/2020 |
| WO | WO-2020120697 A1 | 6/2020 |
| WO | WO-2021030262 A1 | 2/2021 |
| WO | WO-2022177974 A1 | 8/2022 |
| WO | WO-2022177988 A1 | 8/2022 |

OTHER PUBLICATIONS

Berge et al. Pharmaceutical Salts. Journal of Pharmaceutical Sciences 66(1):1-19 (Jan. 1977).

Brazeau et al. Hypothalamic polypeptide that inhibits the secretion of immunoreactive pituitary growth hormone. Science 179:77-79 (1973).

Corda et al. Treatment with long-acting lanreotide autogel in early infancy in patients with severe neonatal hyperinsulinism. Orphanet J Rare Dis. 12(1):108 (2017).

Crider. Somatostatin receptor agonists and antagonists. Expert Opinion on Therapeutic Patents 13(9):1427-1441 (2003).

De Cosio et al. Current and emerging agents for the treatment of hypoglycemia in patients with congenital hyperinsulinism. Paediatr Drugs 21(3):123-136 (2019).

De Leon et al. Congenital hypoglycemia disorders: new aspects of etiology, diagnosis, treatment and outcomes: highlights of the proceedings of the Congenital Hypoglycemia Disorders Symposium, Philadelphia Apr. 2016. Pediatr Diabetes 18(1):3-9 (2017).

(Continued)

*Primary Examiner* — Timothy R Rozof
(74) *Attorney, Agent, or Firm* — WILSON SONSINI GOODRICH & ROSATI

(57) ABSTRACT

Described herein are crystalline forms of 4-[(3S)-3-amino-pyrrolidin-1-yl]-6-cyano-5-(3,5-difluorophenyl)-N-[(2S)-1,1,1-trifluoropropan-2-yl]pyridine-3-carboxamide, uses of such crystalline forms in the preparation of pharmaceutical compositions for the treatment of diseases or conditions that would benefit by administration with a somatostatin modulator compound.

29 Claims, 16 Drawing Sheets

(56) References Cited

OTHER PUBLICATIONS

Esch et al. Primary structure of ovine hypothalamic somatostatin-28 and somatostatin-25. PNAS USA 77:6827-6831 (1980).
Ferrara et al. Biomarkers of insulin for the diagnosis of hyperinsulinemic hypoglycemia in infants and children. J Pediatr 168:212-219 (2016).
Fowler et al. Discovery and Identification of Late Stage, Selective, Nonpeptide, Somatostatin Subtype 5 (Sst5) Agonists for the Treatment of Hyperinsulinemic Hypoglycemia. Poster #MON-089. ENDO Online 2020. Jun. 8-22, 2020.
Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).
Liu et al. Nonpeptide somatostatin agonists with sst4 selectivity: synthesis and structure-activity relationships of thioureas. J Med Chem 41(24):4693-705 (1998).
Lord et al. Hyperinsulinism in the neonate. Clin Perinatol. 45(1):61-74 (2018).
Mallinger et al. Discovery of Potent, Orally Bioavailable, Small-Molecule Inhibitors of WNT Signaling from a Cell-Based Pathway Screen. J Med Chem 58(4):1717-35 (2015).
Ortiz-Marciales et al. Catalytic enantioselective borane reduction of benzyl oximes: preparation of (S)-1-Pyridin-3-YL-Ethylamine Bis Hydrochloride. Organic Synth. 87:36-52 (2010).
Patel et al. Somatostatin receptors. Trends Endocrinol Metab 8:398-405 (1997).
Pradayrol et al. N-terminally extended somatostatin: the primary structure of somatostatin-28. FEBS Letters 109:55-58 (1980).
Reisine et al. Molecular biology of somatostatin receptors. Endocr Rev 16:427-442 (1995).
Rico-Bautista et al. Selective somatostatin 5 (SST5) and somatostatin 2 (SST2) nonpeptide agonists potently suppress glucose- and tolbutamide-stimulated dynamic insulin secretion from isolated human islets. Poster #8684 (2021).
Salomon-Estebanez et al. Conservatively treated congenital hyperinsulinism (CHI) due to K-ATP channel gene mutations: reducing severity overtime. Orphanet J Rare Dis. 11(1):163 (2016).
Science IP Report. Chemical Structure Search (May 24, 2016) (311 pgs.).
Stanley. Perspective on the genetics and diagnosis of congenital hyperinsulinism disorders. J Clin Endocrinol Metab. 101(3):815-826 (2016).
Sturchler et al. Selective Nonpeptide Somatostatin Receptor Subtype 5 (sst5) Agonists Suppress Glucose- and Sulfonylurea-induced Insulin Secretion in Rats. Poster. ENDO 2019. Mar. 23-26, 2019; New Orleans.
Thornton et al. Recommendations from the Pediatric Endocrine Society for Evaluation and Management of Persistent Hypoglycemia in Neonates, Infants, and Children. J Pediatr. 167(2):238-245 (2015).
Van Der Steen et al. A Multicenter experience with long-acting somatostatin analogues in patients with congenital hyperinsulinism. Horm Res Paediatr. 89(2):82-89 (2018).
Wang et al. The effect of global SSTR5 gene ablation on the endocrine pancreas and glucose regulation in aging mice. J Surg Res. 129(1):64-72 (2005).
Weckbecker et al. Opportunities in somatostatin research: biological, chemical and therapeutic aspects. Nat Rev Drug Discov 2(12):999-1017 (2003).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).
Zhao et al. Discovery of nonpeptide 3,4-dihydroquinazoline-4-carboxamides as potent and selective sst2 agonists. Bioorg Med Chem Lett 30(17):127391 (2020).
Zhao et al. Discovery of substituted 3H-pyrido[2,3-d]pyrimidin-4-ones as potent, biased, and orally bioavailable sst2 agonist. Bioorg Med Chem Lett 30(21):127496 (2020).

* cited by examiner

CRYSTALLINE FORMS OF A SOMATOSTATIN MODULATOR

CROSS-REFERENCE TO RELATED APPLICATIONS

This application claims the benefit of U.S. Provisional Patent Application No. 63/150,262 filed on Feb. 17, 2021, which is herein incorporated by reference in its entirety.

FIELD OF THE INVENTION

Described herein are crystalline forms of a somatostatin modulator compound, pharmaceutical compositions and medicaments comprising such crystalline forms, and methods of using such crystalline forms in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor or combination thereof, is attractive for the treatment of conditions, diseases, or disorders that would benefit from modulating somatostatin activity.

SUMMARY OF THE INVENTION

The present disclosure relates to solid state forms of the somatostatin modulator compound 4-[(3S)-3-aminopyrrolidin-1-yl]-6-cyano-5-(3,5-difluorophenyl)-N-[(2S)-1,1,1-trifluoropropan-2-yl]pyridine-3-carboxamide. Such forms of 4-[(3S)-3-aminopyrrolidin-1-yl]-6-cyano-5-(3,5-difluorophenyl)-N-[(2S)-1,1,1-trifluoropropan-2-yl]pyridine-3-carboxamide are useful for modulating the activity of somatostatin receptors in mammals that would benefit from such activity. In some embodiments, the solid state forms of the compound described herein modulate SSTS receptor activity.

Described herein is crystalline 4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1).

In some embodiments, the crystalline form of Compound 1 is crystalline Pattern A of Compound 1. In some embodiments, crystalline Pattern A of Compound 1 is characterized as having:
an X-Ray Powder Diffraction (XRPD) pattern substantially the same as shown in FIG. 1 as measured with Cu Kα1 radiation;
an XRPD pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta as measured with Cu Kα1 radiation;
a DSC thermogram substantially the same as shown in: FIG. 2; or FIG. 3;
a Differential Scanning calorimetry (DSC) thermogram with:
  i. an endotherm having onset at about 96.5° C. and peak at about 106.0° C.; or
  ii. an endotherm having onset at about 86.6° C. and peak at about 101.4° C.;
a Thermogravimetric Analysis (TGA) pattern substantially the same as shown in FIG. 3;
a TGA pattern with a w/w loss of about 3.08% from 50 to 145° C.;
reversible water uptake of about 0.7% between 2% and 95% relative humidity;
an unchanged XRPD pattern after Dynamic Vapor Sorption (DVS) analysis between 2% and 95% relative humidity;
an unchanged XRPD pattern after storage at 40° C./75% relative humidity for 7 days;
an unchanged XRPD pattern after DSC analysis with thermal cycling from 30° C. to 118° C.;
an XRPD pattern that converts to amorphous material after DSC analysis with thermal cycling from 30° C. to 150° C.; or
unit cell parameters substantially equal to the following at 100 K:

| | |
|---|---|
| Crystal System | Monoclinic |
| Space Group | P2$_1$ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å$^3$) | 988.20(3) |
| Z | 2 |
| Calculated Density (Mg/m$^3$) | 1.537 |
| Absorption coefficient (mm$^{-1}$) | 1.169 |
| F(000) | 472 | or combinations thereof.

In some embodiments, crystalline Pattern A of Compound 1 is characterized as having an XRPD pattern substantially the same as shown in FIG. 1 as measured with Cu Kα1 radiation; or an XRPD pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta as measured with Cu Kα1 radiation.

In some embodiments, crystalline Pattern A of Compound 1 is characterized as having a DSC thermogram substantially the same as shown in FIG. 2; or a DSC thermogram with an endotherm having onset at about 96.5° C. and peak at about 106.0° C.

In some embodiments, crystalline Pattern A of Compound 1 is characterized as having a DSC thermogram substantially the same as shown in FIG. 3; or a DSC thermogram with an endotherm having onset at about 86.6° C. and peak at about 101.4° C.

In some embodiments, crystalline Pattern A of Compound 1 is characterized as having a TGA pattern substantially the same as shown in FIG. 3; or a TGA pattern with a w/w loss of about 3.08% from 50 to 145° C.

In some embodiments, crystalline Pattern A of Compound 1 is characterized as having reversible water uptake of about 0.7% between 2% and 95% relative humidity.

In some embodiments, crystalline Pattern A of Compound 1 is characterized as having an unchanged XRPD pattern after DVS analysis between 2% and 95% relative humidity; an unchanged XRPD pattern after storage at 40° C./75% relative humidity for 7 days; an unchanged XRPD pattern after DSC analysis with thermal cycling from 30° C. to 118°

C.; or an XRPD pattern that converts to amorphous material after DSC analysis with thermal cycling from 30° C. to 150° C.

In some embodiments, crystalline Pattern A of Compound 1 is characterized as having unit cell parameters substantially equal to the following at 100 K:

| Crystal System | Monoclinic |
|---|---|
| Space Group | P2$_1$ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å$^3$) | 988.20(3) |
| Z | 2 |
| Calculated Density (Mg/m$^3$) | 1.537 |
| Absorption coefficient (mm$^{-1}$) | 1.169 |
| F(000) | 472 |

In some embodiments, crystalline Pattern A of Compound 1 is a monohydrate.

In some embodiments, crystalline Pattern A of Compound 1 is substantially free of impurities. In some embodiments, crystalline Pattern A of Compound 1 is substantially free of amorphous Compound A. In some embodiments, crystalline Pattern A of Compound 1 is substantially free of other crystalline patterns of Compound A. In some embodiments, crystalline Pattern A of Compound 1 is substantially free of crystalline Pattern B, crystalline Pattern B, and crystalline Pattern D of Compound 1. In some embodiments, crystalline Pattern A of Compound 1 is at least about 90% pure.

In some embodiments, crystalline Pattern A of Compound 1 is at least about 95%, about 96%, about 97%, about 98%, or about 99% pure. In some embodiments, crystalline Pattern A of Compound 1 is at least about 95% pure. In some embodiments, crystalline Pattern A of Compound 1 is at least about 98% pure. In some embodiments, crystalline Pattern A of Compound 1 is In some embodiments, the crystalline form of Compound 1 is crystalline Pattern B of Compound 1. In some embodiments, crystalline Pattern B of Compound 1 is characterized as having:
  an XRPD pattern substantially the same as shown in FIG. 5;
  a DSC thermogram substantially the same as shown in FIG. 6;
  a DSC thermogram with five broad endothermic events having:
    i. onset at about 46.4° C. and peak at about 75.4° C.;
    ii. onset at about 160.0° C. and peak at about 177.1° C.;
    iii. onset at about 191.4° C. and peak at about 198.3° C.;
    iv. onset at about 238.6° C. and peak at about 256.2° C.; and
    v. onset at about 259.1° C. and peak at about 292.0° C.; or combinations thereof.

In some embodiments, the crystalline form of Compound 1 is crystalline Pattern C of Compound 1. In some embodiments, crystalline Pattern C of Compound 1 is characterized as having an XRPD pattern substantially the same as shown in FIG. 7 as measured with Cu Kα1 radiation.

In some embodiments, the crystalline form of Compound 1 is crystalline Pattern D of Compound 1. In some embodiments, crystalline Pattern D of Compound 1 is characterized as having:
  an XRPD pattern substantially the same as shown in FIG. 8 as measured with Cu Kα1 radiation;
  a DSC thermogram substantially the same as shown in FIG. 9;
  a DSC thermogram with three broad endothermic events having:
    i. onset at about 47.4° C. and peak at about 72.2° C.;
    ii. onset at about 235.1° C. and peak at about 255.3° C.; and
    iii. onset at about 265.5° C. and peak at about 278.8° C.; or combinations thereof.

Also described herein is amorphous 4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1). In some embodiments, amorphous Compound 1 is characterized as having:
  an XRPD pattern showing a lack of crystallinity;
  a DSC thermogram substantially the same as shown in FIG. 11;
  a Thermogravimetric Analysis (TGA) pattern substantially the same as shown in FIG. 11;
  a TGA pattern with a w/w loss of about 1.2% from 25 to 190° C.; or combinations thereof.

Also described herein, in some embodiments, is a pharmaceutical composition comprising a crystalline form Compound 1 and at least one pharmaceutically acceptable excipient. In other embodiments, is a pharmaceutical composition comprising amorphous Compound 1 and at least one pharmaceutically acceptable excipient. In some embodiments, the pharmaceutical composition is formulated for administration to a mammal by oral administration. In some embodiments, the pharmaceutical composition is formulated for administration to a mammal by oral administration in the form of a tablet, a pill, a capsule, a suspension, or a solution. In some embodiments, the pharmaceutical composition is in the form of a solid form pharmaceutical composition. In some embodiments, the pharmaceutical composition is in the form of a tablet, a pill, or a capsule.

Also described herein is a process for the preparation of crystalline Pattern A of Compound 1:

(Compound 1)

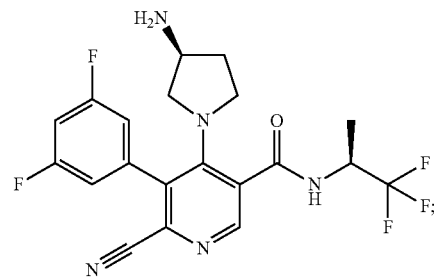

comprising:
  (1) contacting Compound 1 with a suitable solvent to form a slurry; and
  (2) filtering the slurry to obtain crystalline Pattern A of Compound 1.

In some embodiments, the suitable solvent in step (1) is water, isopropanol, tetrahydrofuran, heptane, diethyl ether, or a combination thereof. In some embodiments, the suitable solvent in step (1) is a mixture of water and isopropanol. In some embodiments, the suitable solvent in step (1) comprises from about 10% to about 50% water in isopropanol.

In some embodiments, the suitable solvent in step (1) comprises about 10% water in isopropanol. In some embodiments, the suitable solvent in step (1) is water. In some embodiments, the pH of the slurry is adjusted to pH greater than 8. In some embodiments, the pH of the slurry is adjusted to from about 8 to about 10. In some embodiments, the pH of the slurry is adjusted to from about 9 to about 10. In some embodiments, the pH of the slurry is adjusted to about 10. In some embodiments, the pH of the slurry is adjusted with sodium hydroxide.

In some embodiments, the process further comprises drying the crystalline Pattern A of Compound 1 obtained in step (2) under static vacuum at about 50° C.

Also described herein is a process for the preparation of the free base of Compound 1:

(Compound 1)

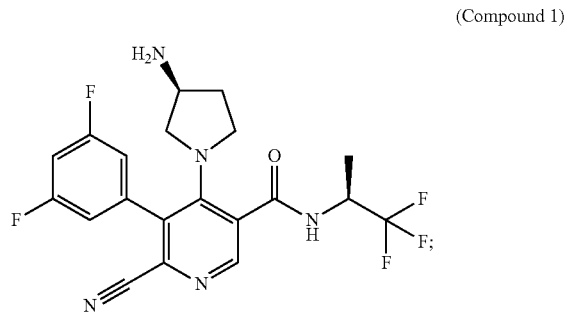 [SMILES: C[C@H](NC(=O)c1cnc(C#N)c(-c2cc(F)cc(F)c2)c1N1CC[C@H](N)C1)C(F)(F)F]

comprising:
(1) contacting tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (Compound 1a):

(Compound 1a)

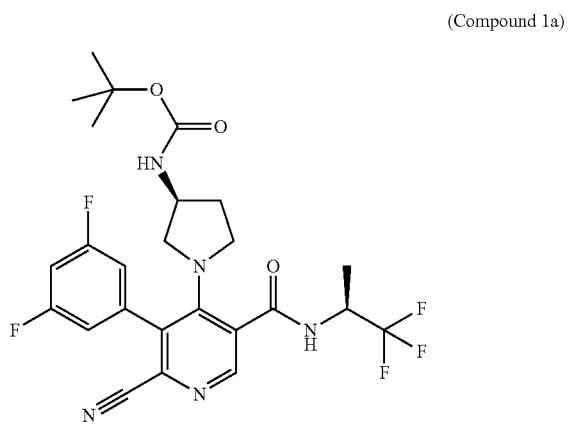 [SMILES: C[C@H](NC(=O)c1cnc(C#N)c(-c2cc(F)cc(F)c2)c1N1CC[C@H](NC(=O)OC(C)(C)C)C1)C(F)(F)F]

with a suitable acid and in a suitable solvent to provide an acid addition salt of Compound 1; and
(2) contacting the acid addition salt of Compound 1 with a suitable base in a suitable solvent to provide Compound 1.

In some embodiments, the suitable solvent in step (1) is dichloromethane, chloroform, dioxane, toluene, hexanes, heptane, methyl tert-butyl ether, diethyl ether, isopropanol, ethanol, methanol, ethyl acetate, isopropyl acetate, acetonitrile, water, or combinations thereof. In some embodiments, the suitable solvent in step (1) is dioxane.

In some embodiments, the suitable acid in step (1) is trifluoroacetic acid, hydrochloric acid, or phosphoric acid. In some embodiments, the suitable acid in step (1) is hydrochloric acid. In some embodiments, the acid addition salt of compound 1 formed in step (1) is the dihydrochloride salt of Compound 1.

In some embodiments, the suitable solvent in step (2) is dichloromethane, chloroform, toluene, methyl tert-butyl ether, diethyl ether, ethyl acetate, water, or combinations thereof. In some embodiments, the suitable solvent in step (2) is a combination of water and ethyl acetate. In some embodiments, the suitable base in step (2) is sodium hydroxide, lithium hydroxide, calcium hydroxide, sodium bicarbonate, potassium bicarbonate, or ammonium hydroxide. In some embodiments, the suitable base in step (2) is sodium hydroxide.

In some embodiments, the process further comprises adjusting the pH of the mixture formed in step (2) to greater than 8. In some embodiments, the process further comprises adjusting the pH of the mixture formed in step (2) to from about 8 to about 10. In some embodiments, the process further comprises adjusting the pH of the mixture formed in step (2) to from about 9 to about 10. In some embodiments, the process further comprises adjusting the pH of the mixture formed in step (2) to about 10.

In some embodiments, the process further comprises drying the isolated Compound 1 obtained in step (2) under static vacuum at about 50° C.

In some embodiments, the isolated Compound 1 is obtained as crystalline Pattern A of Compound 1.

In some embodiments, the process further comprises (3) contacting Compound 1 provided in step (2) with a suitable solvent to form a slurry; and (4) filtering the slurry to obtain crystalline Pattern A of Compound 1.

Articles of manufacture, which include packaging material, a compound described herein, within the packaging material, and a label that indicates that the compound or composition, pharmaceutically active metabolite, or pharmaceutically acceptable solvate thereof, is used for modulating somatostatin activity, or for the treatment, prevention or amelioration of one or more symptoms of a disease or condition that would benefit from modulation of somatostatin activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
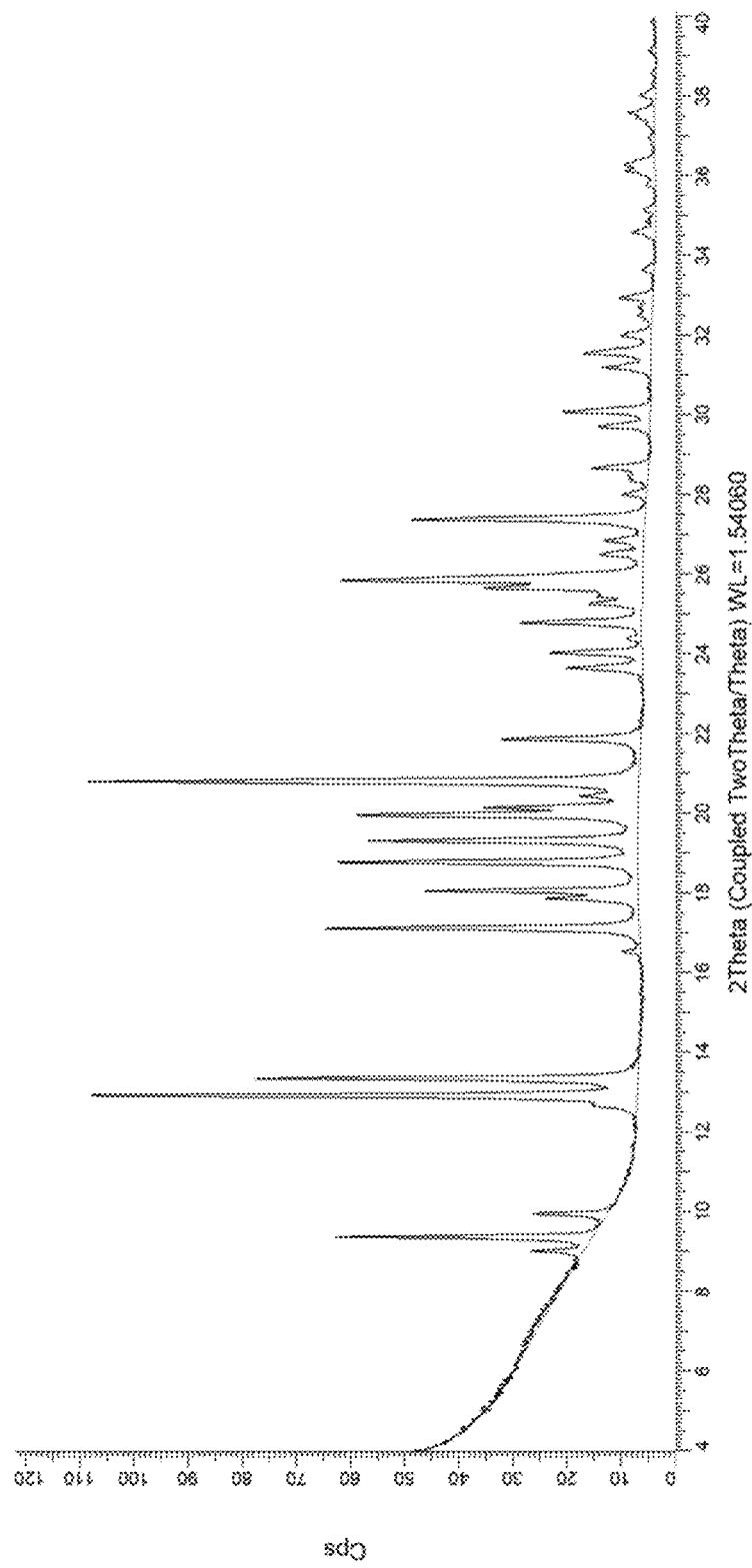
FIG. 1 illustrates a representative X-Ray Powder Diffraction (XRPD) pattern for crystalline Pattern A of Compound 1 as measured with Cu Kα1 radiation.

4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1) is a potent, selective and orally bioavailable somatostatin (SST) modulator. SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut and have multiple functions including modulation of secretion of growth hormone (GH), insulin, glucagon, as well as many other hormones that are anti-proliferative. These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily.

It is possible to selectively modulate any one of the somatostatin receptor subtypes, or combination thereof. In some embodiments, selectively modulating any one of the somatostatin receptor subtypes relative to the other somatostatin receptor subtypes reduces unwanted side effects in a variety of clinical applications.

In some embodiments, SSTR5 agonists are used to treat hyperinsulinemia in a mammal. Hyperinsulinemia leads to several conditions, such as but not limited to, hypoglycemia or low blood sugar, diabetes or uncontrolled blood sugar that fluctuates between a low and high level, increased risk of Polycystic Ovarian Syndrome (PCOS), increased production of very low-density lipoproteins (VLDLs) (referred to as hypertriglyceridemia), increased risk of cardiovascular or heart disease, coronary artery disease (the high insulin level damages the endothelial cells that line the coronary arteries), hypertension or high blood pressure, underactive thyroid gland, weight gain and lethargy.

Compound 1 is a potent, drug-like, selective, nonpeptide, SST5 receptor agonists designed to suppress insulin secretion and prevent the hypoglycemia observed in hyperinsulinemic hypoglycemia.

Compound 1 is a SSTR5 agonist that is useful in the treatment of any one of the conditions, diseases, or disorders described herein.

Compound 1

Compound 1 is a potent small molecule SSTR5 agonist ($EC_{50}$<1 nM) that is selective over other human SST receptor subtypes, and displays >500-fold greater selectivity for SSTR5 over SSTR2.

Compound 1 refers to 4-[(3S)-3-aminopyrrolidin-1-yl]-6-cyano-5-(3,5-difluorophenyl)-N-[(2S)-1,1,1-trifluoropropan-2-yl]pyridine-3-carboxamide, which has the chemical structure shown below.

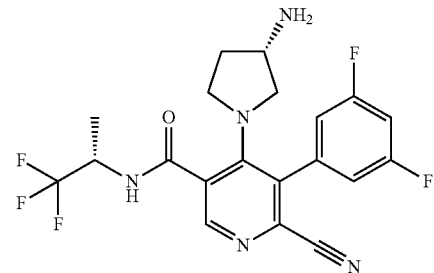 [SMILES: C[C@H](NC(=O)c1cnc(C#N)c(-c2cc(F)cc(F)c2)c1N1CC[C@H](N)C1)C(F)(F)F]

Compound 1 is also referred to as 4-((S)-3-aminopyrrolidin-1-yl)-6-cyano-5-(3,5-difluorophenyl)-N—((S)-1,1,1-trifluoropropan-2-yl)nicotinamide.

In some embodiments, Compound 1 is amorphous.

As used herein, the term "amorphous" or "amorphous solid form" refers to a solid form lacking crystallinity.

In some embodiments, Compound 1 is crystalline.

In some embodiments provided herein, Compound 1 is a single crystalline form. In some embodiments provided herein, Compound 1 is a single crystalline form that is substantially free of any other crystalline form. In some embodiments, the crystalline solid form is a single solid state form, e.g. crystalline Pattern A. In some embodiments, "substantially free" means less than about 10% w/w, less than about 9% w/w, less than about 8% w/w, less than about 7% w/w, less than about 6% w/w, less than about 5% w/w, less than about 4% w/w, less than about 3% w/w, less than about 2.5% w/w, less than about 2% w/w, less than about 1.5% w/w, less than about 1% w/w, less than about 0.75% w/w, less than about 0.50% w/w, less than about 0.25% w/w, less than about 0.10% w/w, or less than about 0.05% w/w of any other crystalline form (e.g., crystalline Pattern B, Pattern C, and/or Pattern D) in a sample of crystalline Pattern 1. In some embodiments, "substantially free" means an undetectable amount (e.g., by XRPD analysis).

In some embodiments, crystallinity of a solid form is determined by methods known in the art. In some embodiments, crystallinity of a solid form is determined by X-Ray Powder Diffraction (XRPD).

Amorphous Compound 1

Figure 11:
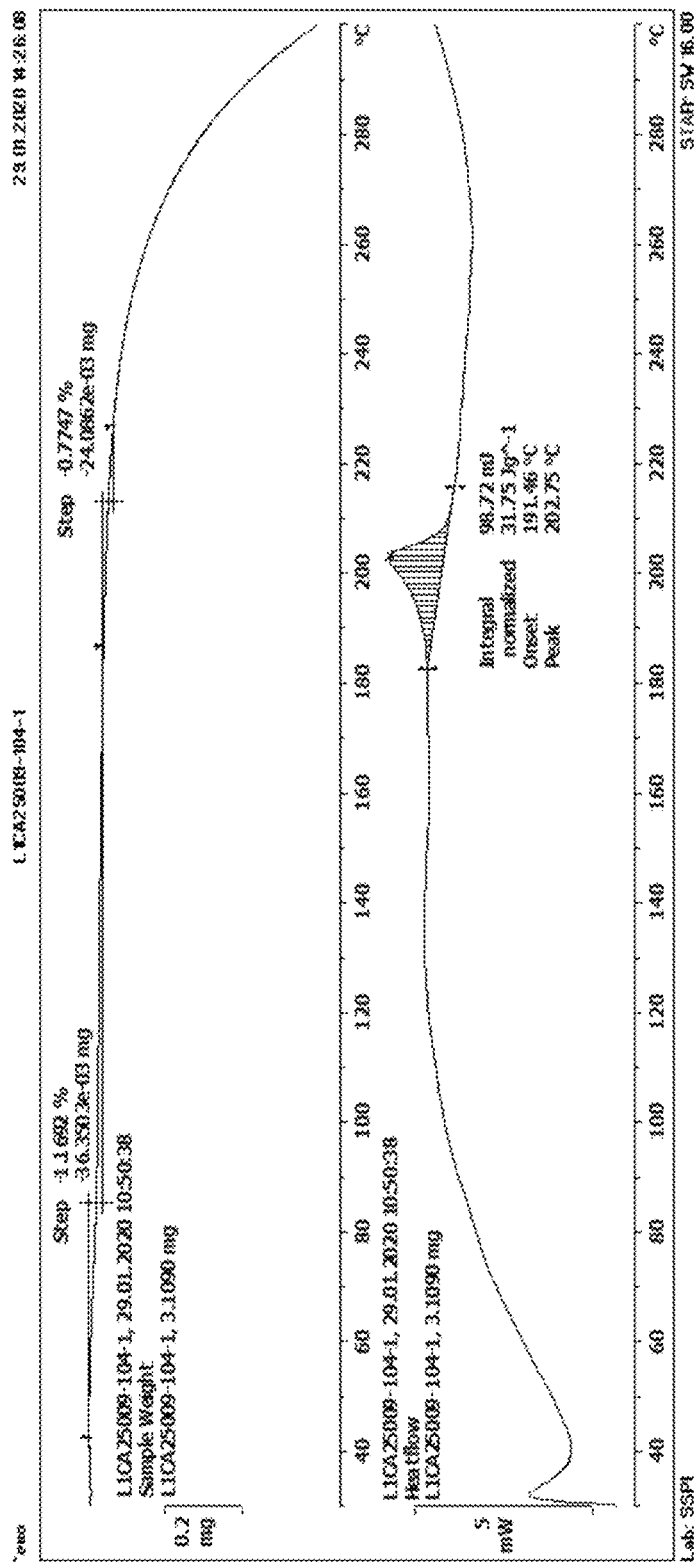
FIG. 11 illustrates a representative simultaneous Thermogravimetric Analysis (TGA) and DSC thermogram for amorphous Compound 1.

Provided herein is the amorphous Compound 1. Some embodiments provide a composition comprising amorphous Compound 1. In some embodiments, amorphous Compound 1 has one of the following properties:
- an XRPD pattern showing a lack of crystallinity;
- a DSC thermogram substantially the same as shown in FIG. 11;
- a TGA pattern substantially the same as shown in FIG. 11;
- a TGA pattern with a w/w loss of about 1.2% from 25 to 190° C.;
- or combinations thereof.

In some embodiments, amorphous Compound 1 has an XRPD pattern showing a lack of crystallinity. In some embodiments, amorphous Compound 1 has a DSC thermogram substantially the same as shown in FIG. 11. In some embodiments, amorphous Compound 1 has a TGA pattern substantially the same as shown in FIG. 11. In some embodiments, amorphous Compound 1 has a TGA pattern with a w/w loss of about 1.2% from 25 to 190° C.

In some embodiments, amorphous Compound 1 is substantially free of impurities. In some embodiments, amorphous Compound 1 is at least about 90% pure. In some embodiments, amorphous Compound 1 is at least about 95%, about 96%, about 97%, about 98%, or about 99% pure. In some embodiments, amorphous Compound 1 is at least about 95% pure. In some embodiments, amorphous Compound 1 is at least about 96% pure. In some embodiments, amorphous Compound 1 is at least about 97% pure. In some embodiments, amorphous Compound 1 is at least about 98% pure. In some embodiments, amorphous Compound 1 is at least about 99% pure. In some embodiments, amorphous Compound 1 is at least about 99.1%, about 99.2%, about 99.3%, about 99.4%, about 99.5%, about 99.6%, about 99.7%, about 99.8%, about 99.9%, or about 100% pure.

Figure 12:
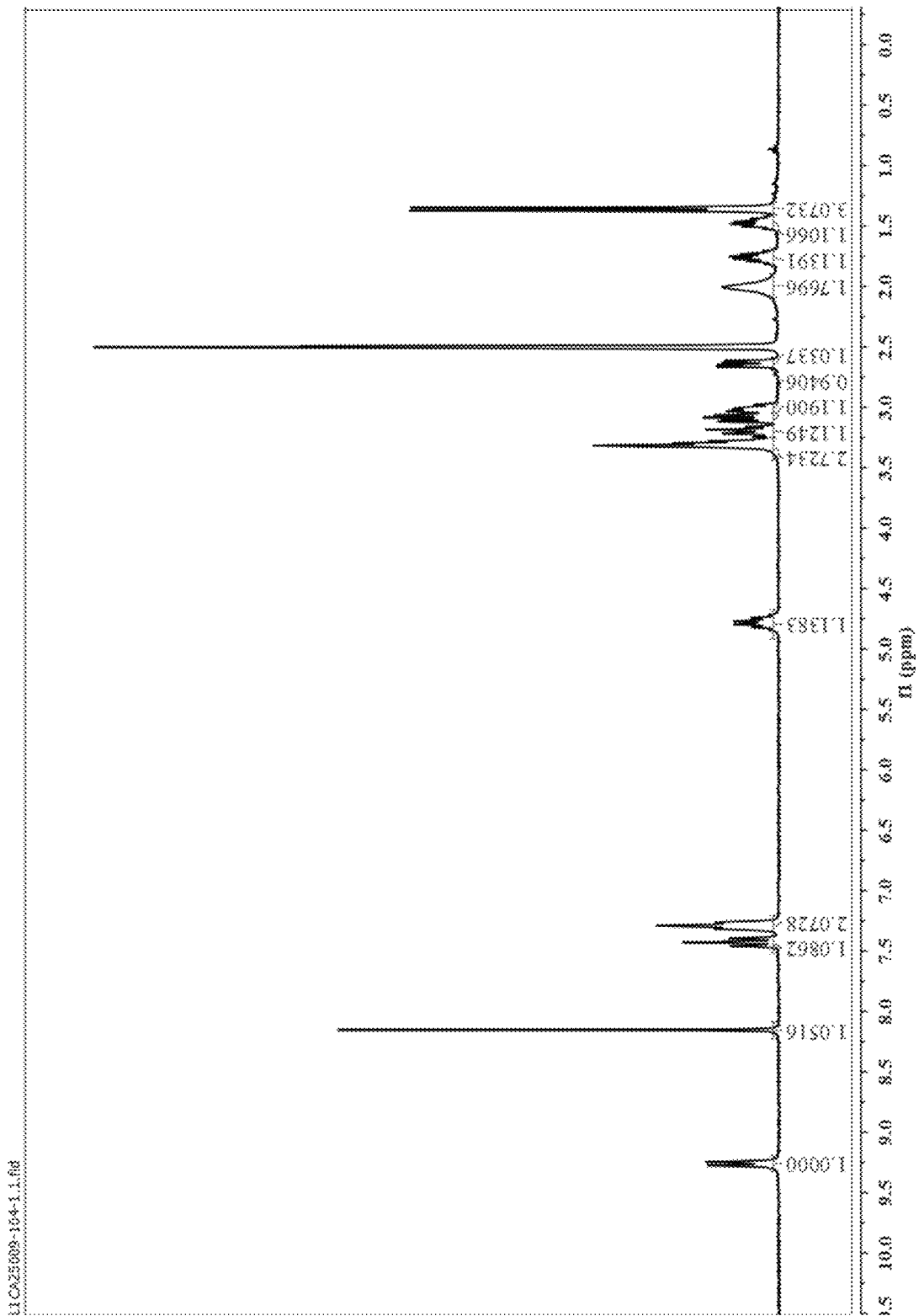
FIG. 12 illustrates a representative NMR spectrum for amorphous Compound 1.

In some embodiments, amorphous Compound 1 has an NMR spectrum substantially the same as shown in FIG. 12.

Crystalline Compound 1

Also provided herein is crystalline Compound 1.

In some embodiments, the crystalline Compound 1 is unsolvated. In some embodiments, the crystalline Compound 1 is anhydrous.

In some embodiments, the crystalline Compound 1 is solvated. In some embodiments, the crystalline Compound 1 is hydrated. In some embodiments, crystalline Pattern A of Compound 1 is a monohydrate.

In some embodiments, the crystalline Compound 1 is substantially free of impurities. In some embodiments, the crystalline Compound 1 is at least about 90% pure. In some embodiments, the crystalline Compound 1 is at least about 95%, about 96%, about 97%, about 98%, or about 99% pure. In some embodiments, the crystalline Compound 1 is at least about 95% pure. In some embodiments, the crystalline Compound 1 is at least about 96% pure. In some embodiments, the crystalline Compound 1 is at least about 97% pure. In some embodiments, the crystalline Compound 1 is at least about 98% pure. In some embodiments, the crystalline Compound 1 is at least about 99% pure. In some embodiments, the crystalline Compound 1 is at least about 99.1%, about 99.2%, about 99.3%, about 99.4%, about 99.5%, about 99.6%, about 99.7%, about 99.8%, about 99.9%, or about 100% pure.

Crystalline Pattern A of Compound 1

Figure 2:
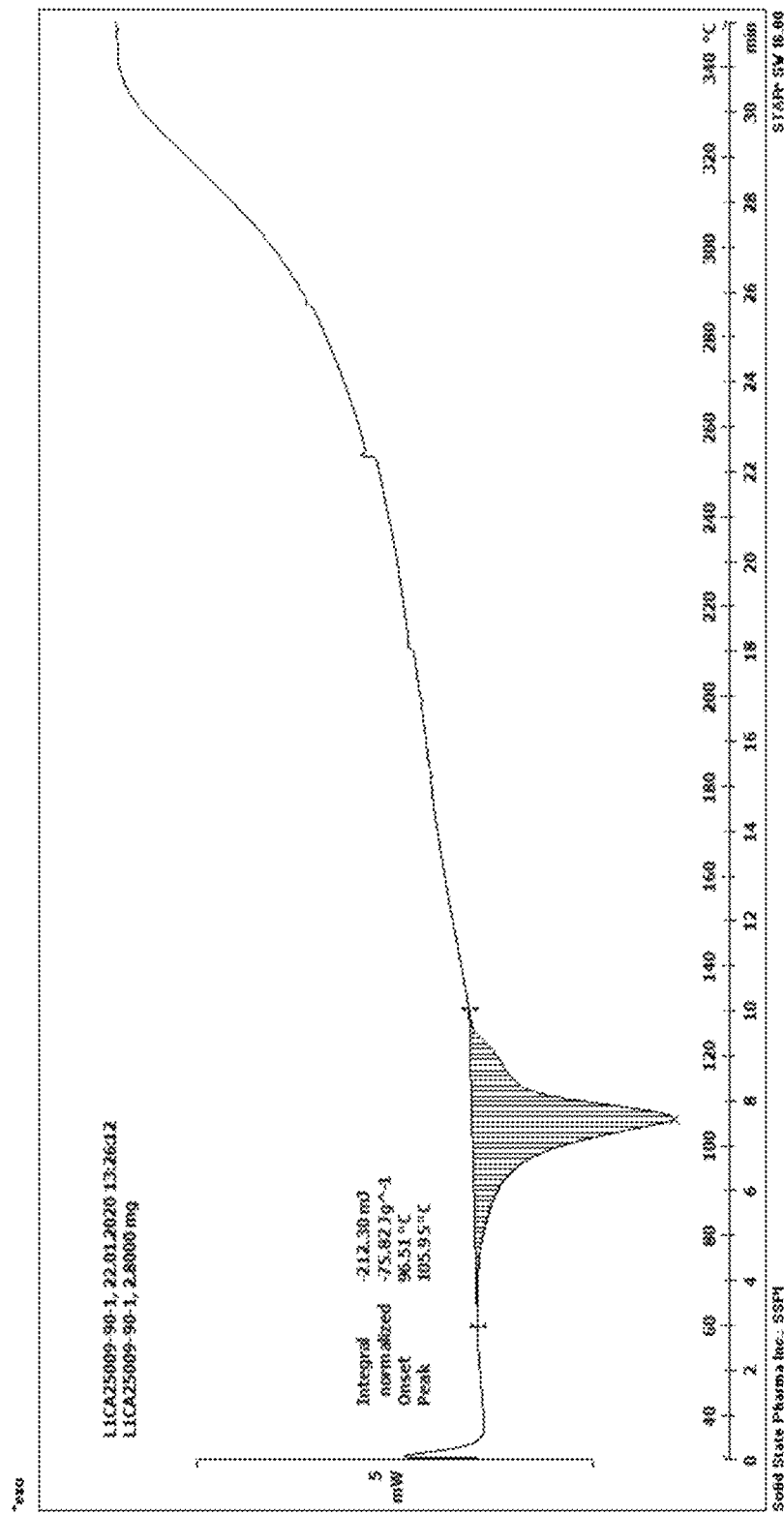
FIG. 2 illustrates a representative standalone Differential Scanning calorimetry (DSC) thermogram for crystalline Pattern A of Compound 1.
Figure 3:
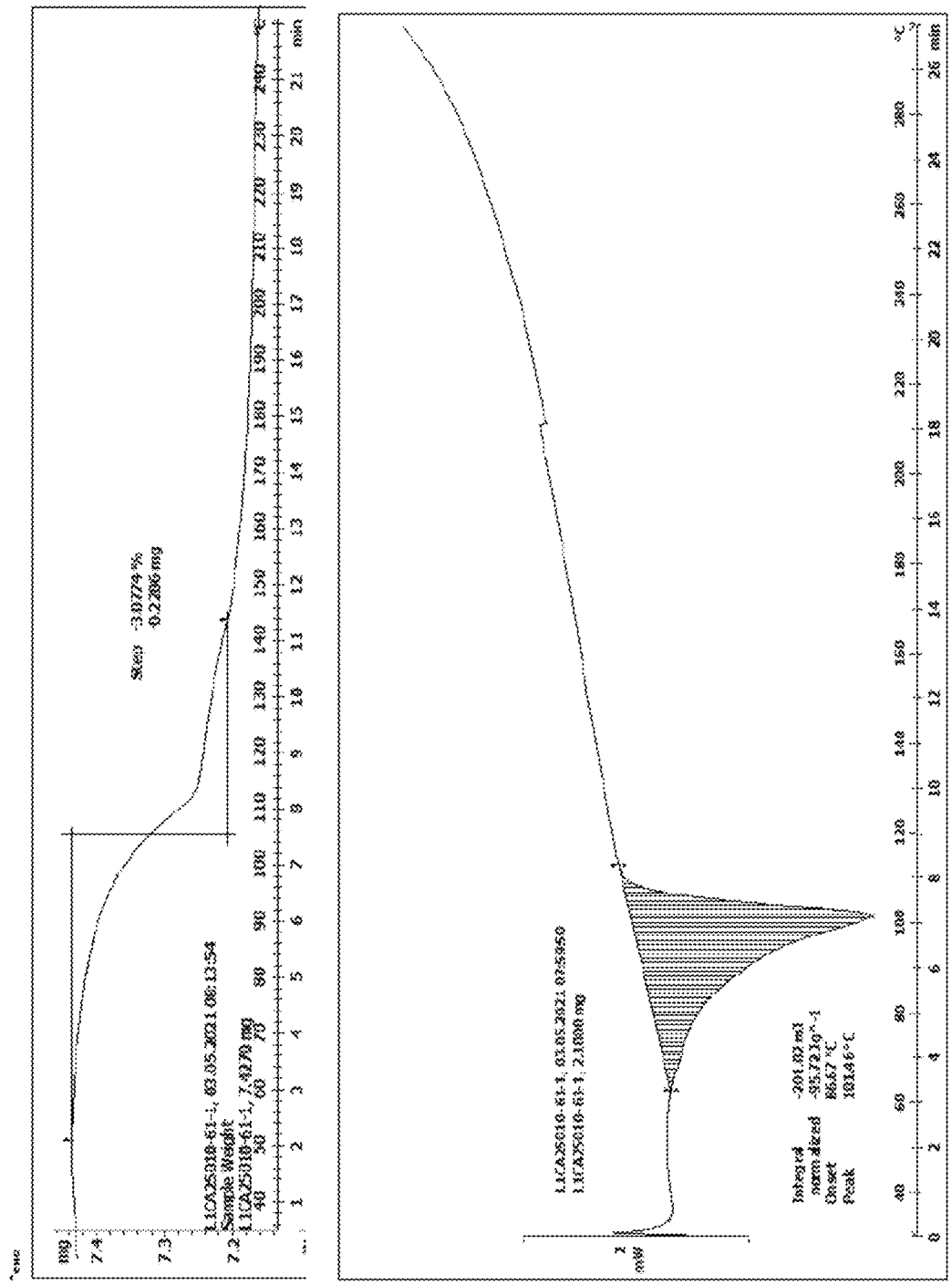
FIG. 3 illustrates a representative Thermogravimetric Analysis (TGA) and DSC thermogram for crystalline Pattern A of Compound 1.

In some embodiments, the crystalline Compound 1 is crystalline Pattern A of Compound 1. In some embodiments, described herein is a composition comprising crystalline Pattern A of Compound 1. In some embodiments, crystalline Pattern A of Compound 1 is characterized as having:
- an XRPD pattern substantially the same as shown in FIG. 1 as measured with Cu Kα1 radiation;
- an XRPD pattern with peaks at about 9.4° 2-Theta, about 12.9° 2-Theta, about 13.3° 2-Theta, about 17.1° 2-Theta, about 18.8° 2-Theta, about 19.3° 2-Theta, and about 20.7° 2-Theta as measured with Cu Kα1 radiation;
- a DSC thermogram substantially the same as shown in: FIG. 2; or FIG. 3;
- a DSC thermogram with:
  - an endotherm having onset at about 96.5° C. and peak at about 106.0° C.; or
  - an endotherm having onset at about 86.6° C. and peak at about 101.4° C.;
- a TGA pattern substantially the same as shown in FIG. 3;
- a TGA pattern with a w/w loss of about 3.08% from 50 to 145° C.;
- reversible water uptake of about 0.7% between 2% and 95% relative humidity;
- an unchanged XRPD pattern after Dynamic Vapor Sorption (DVS) analysis between 2% and 95% relative humidity;
- an unchanged XRPD pattern after storage at 40° C./75% relative humidity for 7 days;
- an unchanged XRPD pattern after DSC analysis with thermal cycling from 30° C. to 118° C.;
- an XRPD pattern that converts to amorphous material after DSC analysis with thermal cycling from 30° C. to 150° C.; or
- unit cell parameters substantially equal to the following at 100 K:

| | |
|---|---|
| Crystal System | Monoclinic |
| Space Group | P2$_1$ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å$^3$) | 988.20(3) |
| Z | 2 |
| Calculated Density (Mg/m$^3$) | 1.537 |
| Absorption coefficient (mm$^{-1}$) | 1.169 |
| F(000) | 472 | or combinations thereof.

In some embodiments, crystalline Pattern A of Compound 1 has an XRPD pattern substantially the same as shown in FIG. 1. In some embodiments, crystalline Pattern A of Compound 1 has an XRPD pattern with peaks at about 9.4° 2-Theta, about 12.9° 2-Theta, about 13.3° 2-Theta, about 17.1° 2-Theta, about 18.8° 2-Theta, about 19.3° 2-Theta, and about 20.7° 2-Theta. In some embodiments, crystalline Pattern A of Compound 1 has a DSC thermogram substantially the same as shown in FIG. 2. In some embodiments, crystalline Pattern A of Compound 1 has a DSC thermogram with an endotherm having onset at about 96.5° C. and peak at about 106.0° C. In some embodiments, crystalline Pattern A of Compound 1 has a DSC thermogram substantially the same as shown in FIG. 3. In some embodiments, crystalline Pattern A of Compound 1 has a DSC thermogram with an endotherm having onset at about 86.6° C. and peak at about 101.4° C. In some embodiments, crystalline Pattern A of Compound 1 has a TGA pattern substantially the same as shown in FIG. 3. In some embodiments, crystalline Pattern A of Compound 1 has a TGA pattern with a w/w loss of about 3.08% from 50 to 145° C. In some embodiments, crystalline Pattern A of Compound 1 has reversible water uptake of about 0.7% between 2% and 95% relative humidity. In some embodiments, crystalline Pattern A of Compound 1 has an unchanged XRPD pattern after DVS analysis between 2% and 95% relative humidity. In some embodiments, crystalline Pattern A of Compound 1 has an unchanged XRPD pattern after storage at 40° C./75% relative humidity for 7 days. In some embodiments, crystalline Pattern A of Compound 1 has an unchanged XRPD pattern after DSC analysis with thermal cycling from 30° C. to 118° C. In some embodiments, crystalline Pattern A of Compound 1 has an XRPD pattern that converts to amorphous material after DSC analysis with thermal cycling from 30° C. to 150° C.

In some embodiments, crystalline Pattern A of Compound 1 is characterized as having unit cell parameters substantially equal to the following at 100 K:

| | |
|---|---|
| Crystal System | Monoclinic |
| Space Group | P2$_1$ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å$^3$) | 988.20(3) |
| Z | 2 |
| Calculated Density (Mg/m$^3$) | 1.537 |
| Absorption coefficient (mm$^{-1}$) | 1.169 |
| F(000) | 472 |

In some embodiments, crystalline Pattern A of Compound 1 has an XRPD pattern reflection at about 20.7° 2-Theta. In some embodiments, crystalline Pattern A is further characterized by at least one XRPD pattern reflection selected from about 9.4° 2-Theta, about 12.9° 2-Theta, about 13.3° 2-Theta, about 17.1° 2-Theta, about 18.8° 2-Theta, and about 19.3° 2-Theta. In some embodiments, crystalline Pattern A is further characterized by at least two XRPD pattern reflections selected from about 9.4° 2-Theta, about 12.9° 2-Theta, about 13.3° 2-Theta, about 17.1° 2-Theta, about 18.8° 2-Theta, and about 19.3° 2-Theta. In some embodiments, crystalline Pattern A is further characterized by at least three XRPD pattern reflections selected from about 9.4° 2-Theta, about 12.9° 2-Theta, about 13.3° 2-Theta, about 17.1° 2-Theta, about 18.8° 2-Theta, and about 19.3° 2-Theta. In some embodiments, crystalline Pattern A is further characterized by XRPD pattern reflections at about 9.4° 2-Theta, about 12.9° 2-Theta, about 13.3° 2-Theta, about 17.1° 2-Theta, about 18.8° 2-Theta, and about 19.3° 2-Theta.

In some embodiments, crystalline Pattern A of Compound 1 has an XRPD pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta.

In some embodiments, crystalline Pattern A of Compound 1 has an XRPD pattern reflection at 20.7±0.2° 2-Theta. In some embodiments, crystalline Pattern A is further characterized by at least one XRPD pattern reflection selected from 9.4±0.2° 2-Theta, 12.9±0.2° 2-Theta, 13.3±0.2° 2-Theta, 17.1±0.2° 2-Theta, 18.8±0.2° 2-Theta, and 19.3±0.2° 2-Theta. In some embodiments, crystalline Pattern A is further characterized by at least two XRPD pattern reflections selected from 9.4±0.2° 2-Theta, 12.9±0.2° 2-Theta, 13.3±0.2° 2-Theta, 17.1±0.2° 2-Theta, 18.8±0.2° 2-Theta, and 19.3±0.2° 2-Theta. In some embodiments, crystalline Pattern A is further characterized by at least three XRPD pattern reflections selected from 9.4±0.2° 2-Theta, 12.9±0.2° 2-Theta, 13.3±0.2° 2-Theta, 17.1±0.2° 2-Theta, 18.8±0.2° 2-Theta, and 19.3±0.2° 2-Theta. In some embodiments, crystalline Pattern A is further characterized by XRPD pattern reflections at 9.4±0.2° 2-Theta, 12.9±0.2° 2-Theta, 13.3±0.2° 2-Theta, 17.1±0.2° 2-Theta, 18.8±0.2° 2-Theta, and 19.3±0.2° 2-Theta.

In some embodiments, crystalline Pattern A of Compound 1 has an XRPD pattern with peaks at 9.4±0.1° 2-Theta, 12.9±0.1° 2-Theta, 13.3±0.1° 2-Theta, 17.1±0.1° 2-Theta, 18.8±0.1° 2-Theta, 19.3±0.1° 2-Theta, and 20.7±0.1° 2-Theta.

In some embodiments, crystalline Pattern A of Compound 1 has an XRPD pattern reflection at 20.7±0.1° 2-Theta. In some embodiments, crystalline Pattern A is further characterized by at least one XRPD pattern reflection selected from 9.4±0.1° 2-Theta, 12.9±0.1° 2-Theta, 13.3±0.1° 2-Theta, 17.1±0.1° 2-Theta, 18.8±0.1° 2-Theta, and 19.3±0.1° 2-Theta. In some embodiments, crystalline Pattern A is further characterized by at least two XRPD pattern reflections selected from 9.4±0.1° 2-Theta, 12.9±0.1° 2-Theta, 13.3±0.1° 2-Theta, 17.1±0.1° 2-Theta, 18.8±0.1° 2-Theta, and 19.3±0.1° 2-Theta. In some embodiments, crystalline Pattern A is further characterized by at least three XRPD pattern reflections selected from 9.4±0.1° 2-Theta, 12.9±0.1° 2-Theta, 13.3±0.1° 2-Theta, 17.1±0.1° 2-Theta, 18.8±0.1° 2-Theta, and 19.3±0.1° 2-Theta. In some embodiments, crystalline Pattern A is further characterized by XRPD pattern reflections at 9.4±0.1° 2-Theta, 12.9±0.1° 2-Theta, 13.3±0.1° 2-Theta, 17.1±0.1° 2-Theta, 18.8±0.1° 2-Theta, and 19.3±0.1° 2-Theta.

Figure 4:
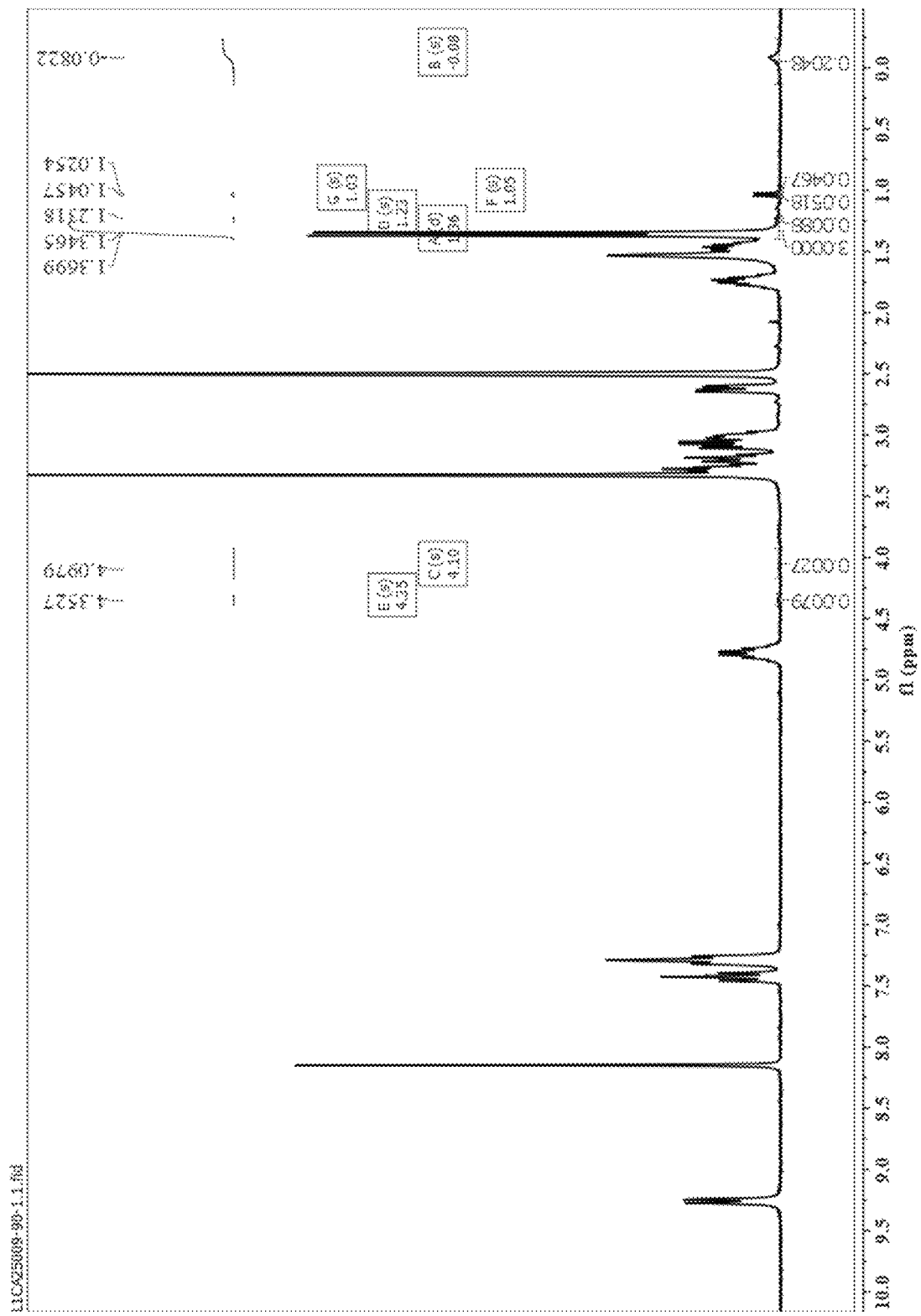
FIG. 4 illustrates a representative NMR spectrum for crystalline Pattern A of Compound 1.

In some embodiments, crystalline Pattern A of Compound 1 has an NMR spectrum substantially the same as shown in FIG. 4.

In some embodiments, crystalline Pattern A of Compound 1 remains stable after solvent milling in isopropyl acetate, water, or methyl isobutyl ketone. In some embodiments, crystallinity of crystalline Pattern A of Compound 1 is lost after dry milling, resulting in amorphous material.

Crystalline Pattern B of Compound 1

In some embodiments, crystalline Compound 1 is crystalline Pattern B of Compound 1. In some embodiments, described herein is a composition comprising crystalline Pattern B of Compound 1. In some embodiments, crystalline Pattern B of Compound 1 is characterized as having:
  an XRPD pattern substantially the same as shown in FIG. 5 as measured with Cu Kα1 radiation;
  a DSC thermogram substantially the same as shown in FIG. 6;
  a DSC thermogram with five broad endothermic events having:
    i. onset at about 46.4° C. and peak at about 75.4° C.;
    ii. onset at about 160.0° C. and peak at about 177.1° C.;
    iii. onset at about 191.4° C. and peak at about 198.3° C.;
    iv. onset at about 238.6° C. and peak at about 256.2° C.; and
    v. onset at about 259.1° C. and peak at about 292.0° C.;
    or combinations thereof.

Figure 5:
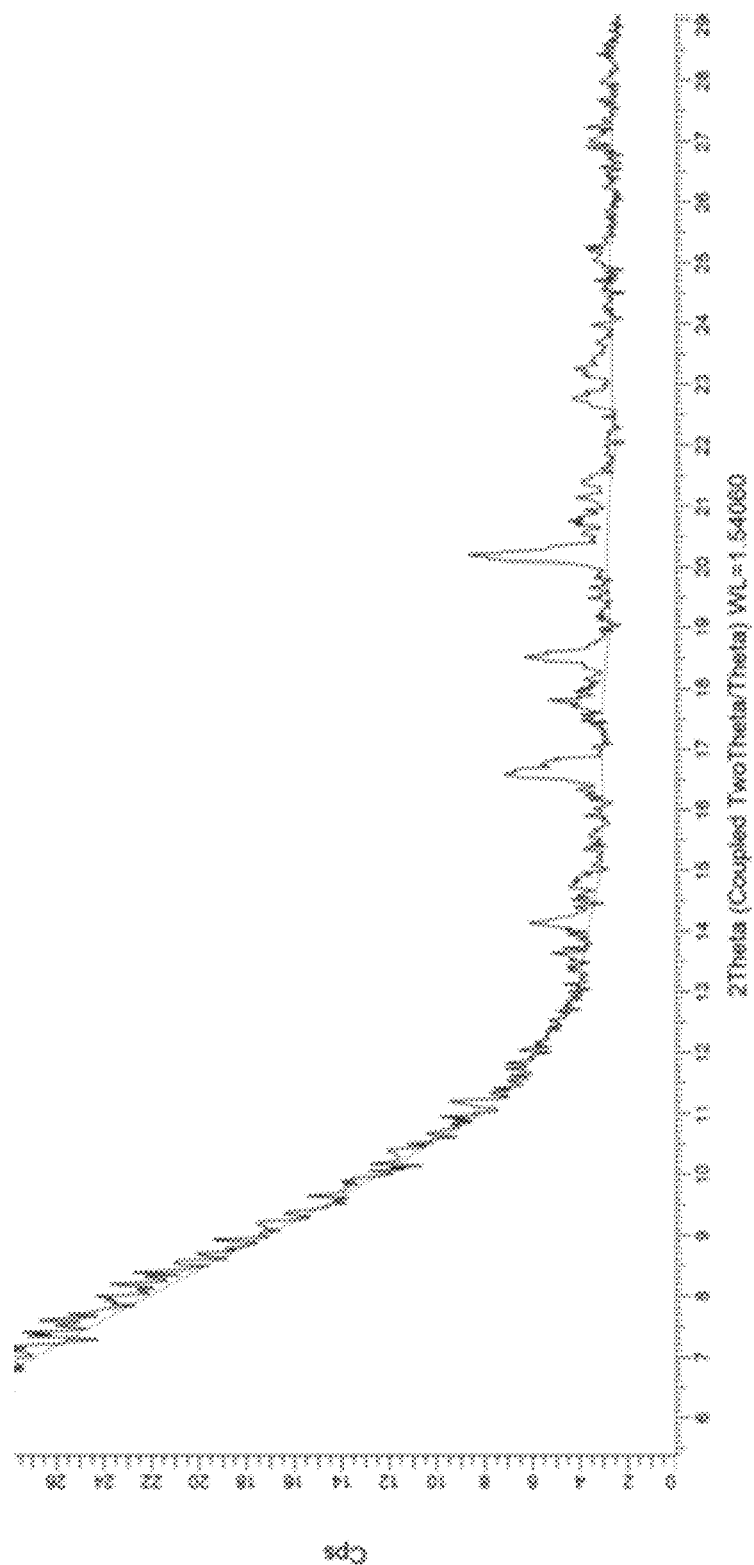
FIG. 5 illustrates a representative XRPD pattern for crystalline Pattern B of Compound 1 as measured with Cu Kα1 radiation.
Figure 6:
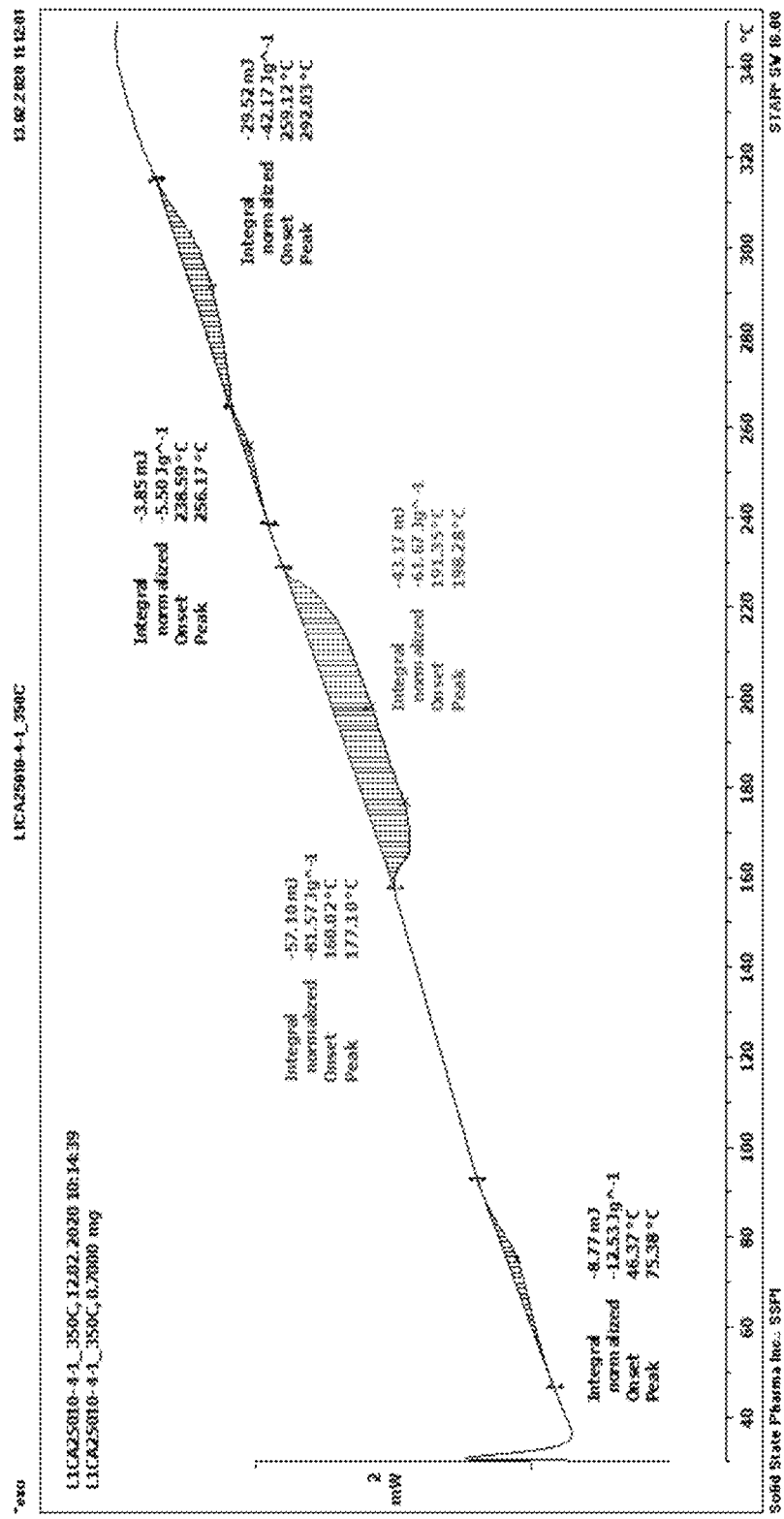
FIG. 6 illustrates a representative standalone DSC thermogram for crystalline Pattern B of Compound 1.

In some embodiments, crystalline Patten B of Compound 1 has an XRPD pattern substantially the same as shown in FIG. 5 as measured with Cu Kα1 radiation. In some embodiments, crystalline Patten B of Compound 1 has a DSC thermogram substantially the same as shown in FIG. 6. In some embodiments, crystalline Patten B of Compound 1 has a DSC thermogram with five broad endothermic events having: onset at about 46.4° C. and peak at about 75.4° C.; onset at about 160.0° C. and peak at about 177.1° C.; onset at about 191.4° C. and peak at about 198.3° C.; onset at about 238.6° C. and peak at about 256.2° C.; and onset at about 259.1° C. and peak at about 292.0° C.

Crystalline Pattern C of Compound 1

Figure 7:
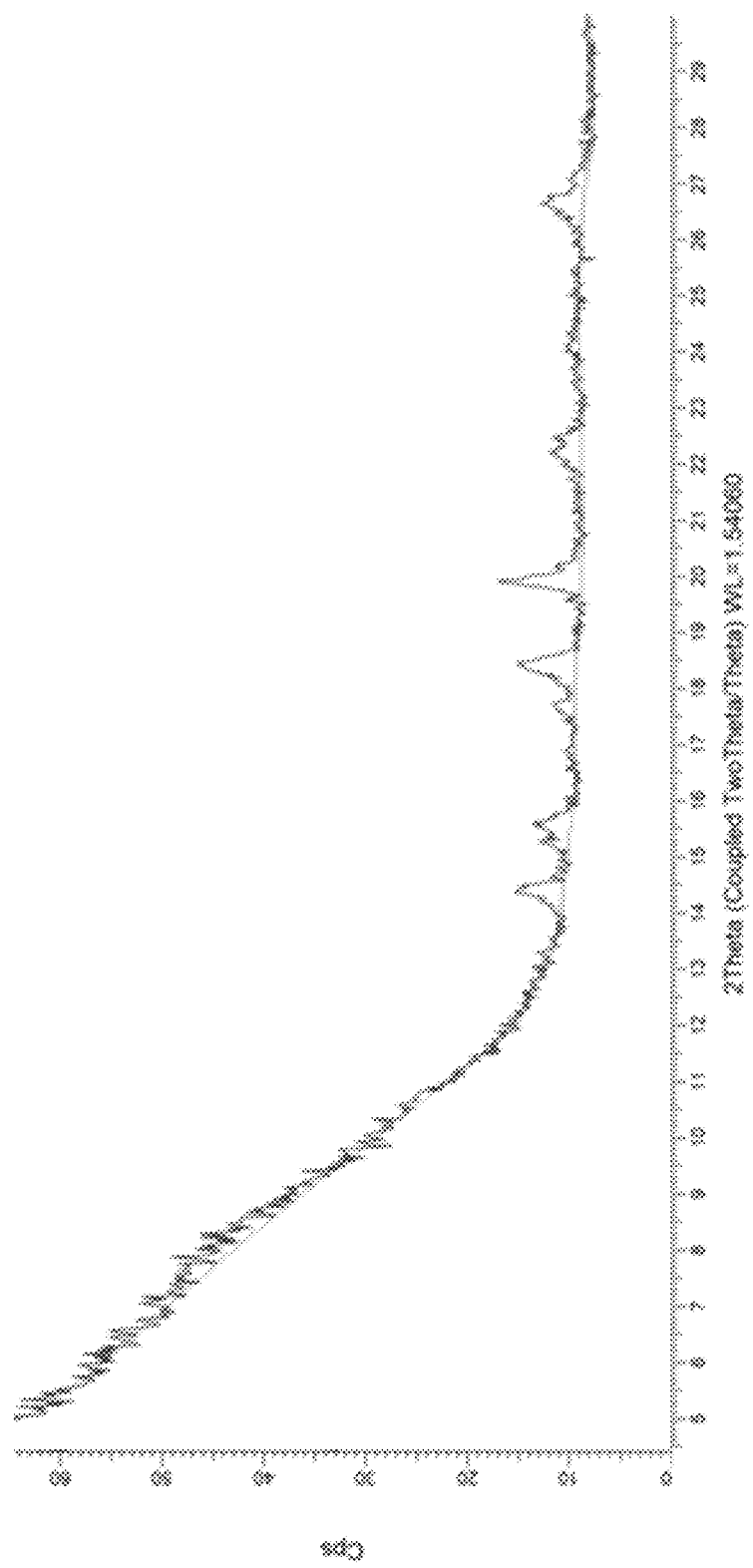
FIG. 7 illustrates a representative XRPD pattern for crystalline Pattern C of Compound 1 as measured with Cu Kα1 radiation.

In some embodiments, crystalline Compound 1 is crystalline Pattern C of Compound 1. In some embodiments, described herein is a composition comprising crystalline Pattern C of Compound 1. In some embodiments, crystalline Pattern C of Compound 1 is characterized as having an XRPD pattern substantially the same as shown in FIG. 7 as measured with Cu Kα1 radiation.

Crystalline Pattern D of Compound 1

In some embodiments, crystalline Compound 1 is crystalline Pattern D of Compound 1. In some embodiments, described herein is a composition comprising crystalline Pattern D of Compound 1. In some embodiments, crystalline Pattern D of Compound 1 is characterized as having:
  an XRPD pattern substantially the same as shown in FIG. 8 as measured with Cu Kα1 radiation;
  a DSC thermogram substantially the same as shown in FIG. 9;
  a DSC thermogram with three broad endothermic events having:
    i. onset at about 47.4° C. and peak at about 72.2° C.;
    ii. onset at about 235.1° C. and peak at about 255.3° C.; and
    iii. onset at about 265.5° C. and peak at about 278.8° C.; or
  combinations thereof.

Figure 8:
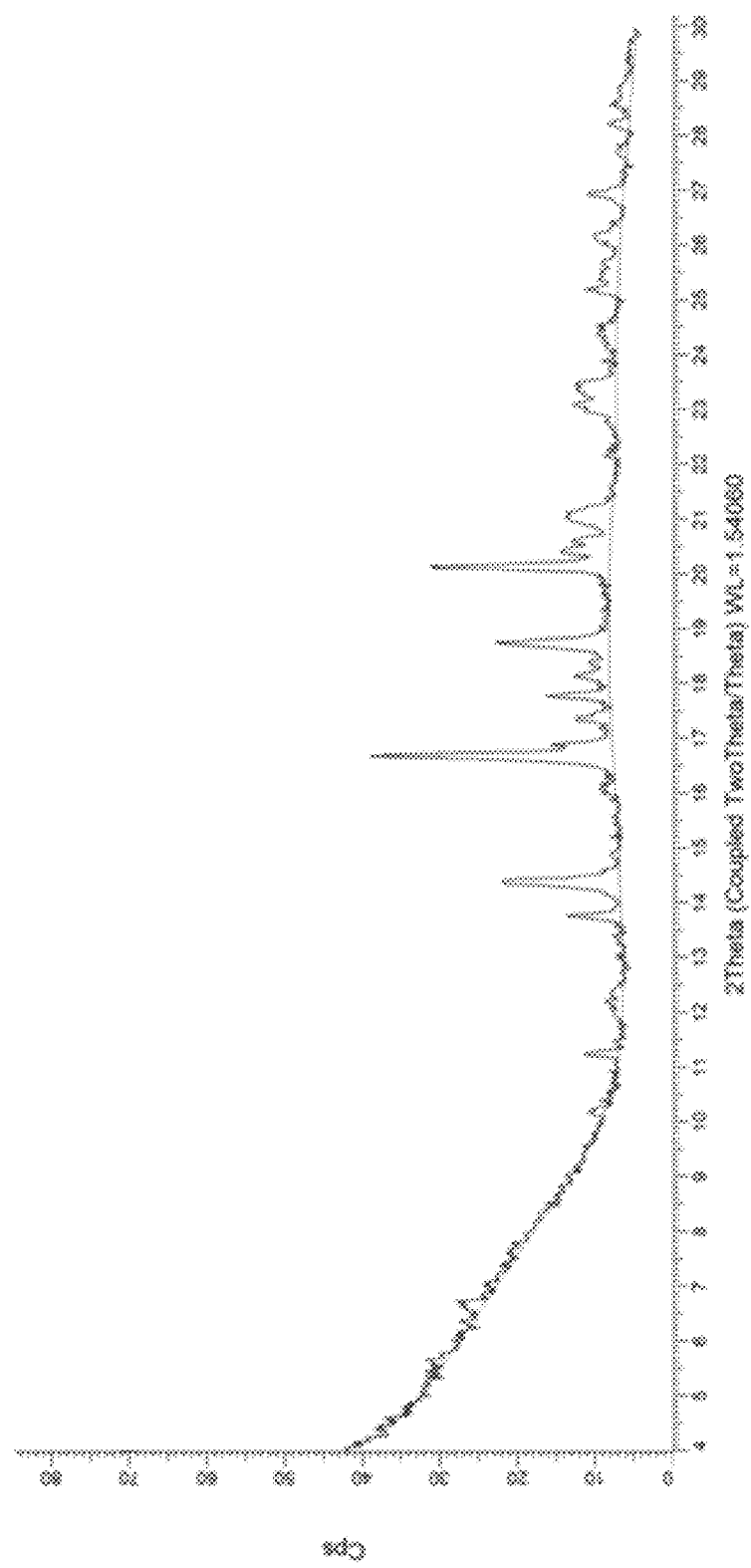
FIG. 8 illustrates a representative XRPD pattern for crystalline Pattern D of Compound 1 as measured with Cu Kα1 radiation.
Figure 9:
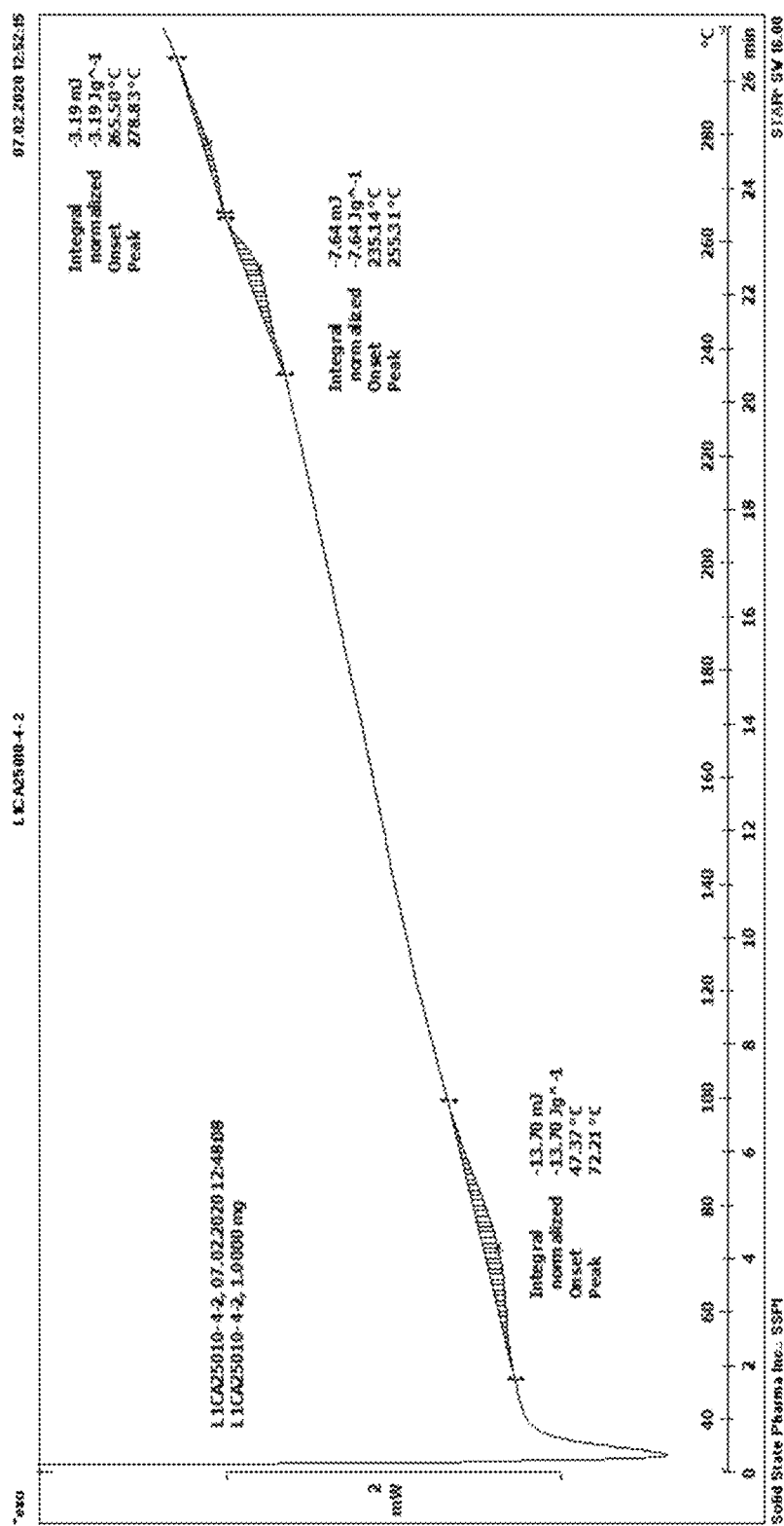
FIG. 9 illustrates a representative standalone DSC thermogram for crystalline Pattern D of Compound 1.

In some embodiments, crystalline Patten D of Compound 1 has an XRPD pattern substantially the same as shown in FIG. 8 as measured with Cu Kα1 radiation. In some embodiments, crystalline Patten D of Compound 1 has a DSC thermogram substantially the same as shown in FIG. 9. In some embodiments, crystalline Patten D of Compound 1 has a DSC thermogram with three broad endothermic events having: onset at about 47.4° C. and peak at about 72.2° C.; onset at about 235.1° C. and peak at about 255.3° C.; and onset at about 265.5° C. and peak at about 278.8° C.

Figure 10:
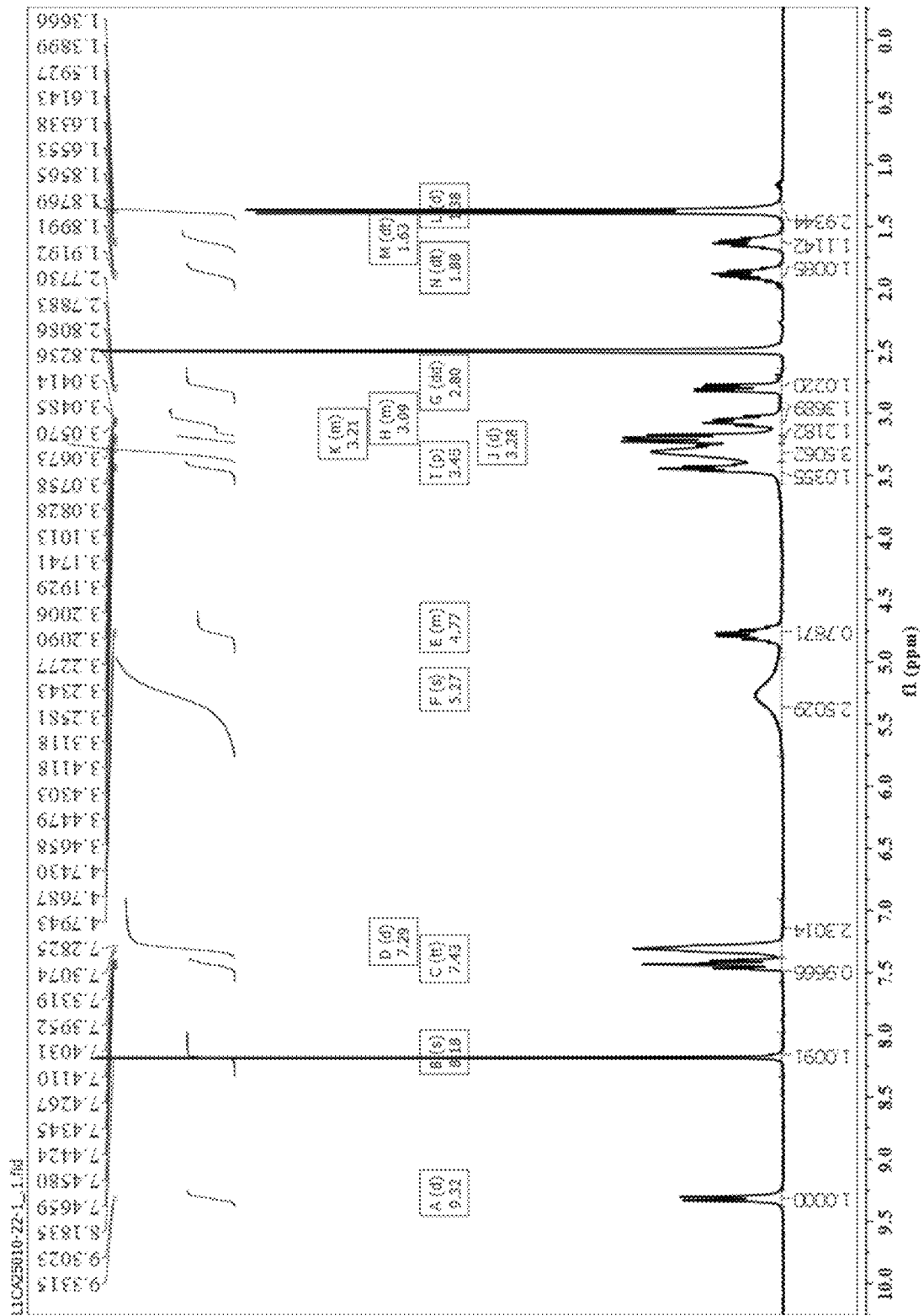
FIG. 10 illustrates a representative NMR spectrum for crystalline Pattern D of Compound 1.

In some embodiments, crystalline Pattern D of Compound 1 has an NMR spectrum substantially the same as shown in FIG. 10. In some embodiments, the NMR spectrum shows that peaks in the aliphatic region are shifted downfield amorphous material. In some embodiments, the NMR spectrum shows that crystalline Pattern D of Compound 1 is a salt.

Methods of Making Compound 1 and Solid State Forms Thereof

Compounds described herein are synthesized using standard synthetic techniques or using methods known in the art in combination with methods described herein. Unless otherwise indicated, conventional methods of mass spectroscopy, NMR, HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In the reactions described, it may be necessary to protect reactive functional groups, for example hydroxy or amino groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, Compound 1 and solid-state forms thereof are prepared as described in the examples.

Synthesis of Compound 1

The preparation of Compound 1 has been previously described (see, PCT/US2020/045610 and U.S. application Ser. No. 16/989,193, each of which is incorporated by reference in its entirety). Treatment of Compound 1a with trifluoroacetic acid yields the bis(2,2,2-trifluoroacetate) salt of Compound 1. Other salts can be prepared depending on the reagents used in the final transformation, and the free base of Compound 1 can prepared, as outlined in Scheme 1.

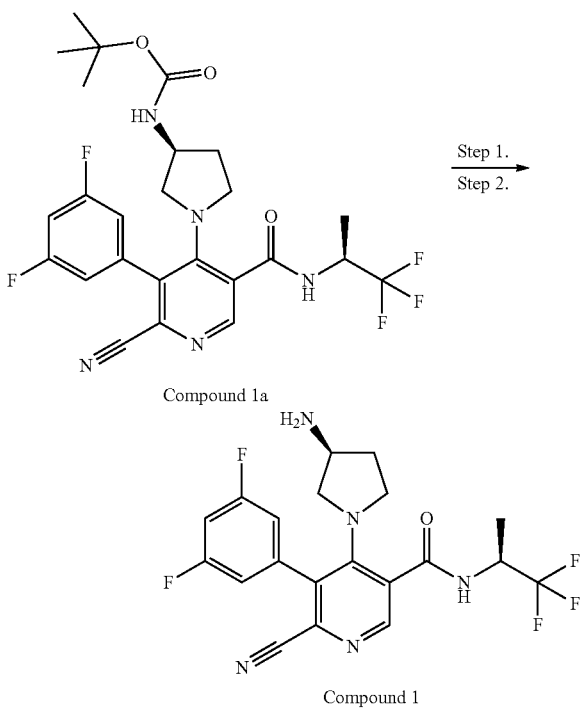

Scheme 1: Preparation of Compound 1

Briefly, in some embodiments, Compound 1a (tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl) carbamate) is reacted with a suitable acid to remove the carbamate protecting group, which yields the acid addition salt of Compound 1. The acid addition salt of Compound 1 is then treated with a suitable base to provide the free base Compound 1.

Step 1: Deprotection of the Boc Protecting Group

In some embodiments, the tert-butyloxycarbonyl protecting group of Compound 1a is removed by contacting Compound 1a with a suitable acid and in a suitable solvent to provide an acid addition salt of Compound 1.

In some embodiments, the suitable solvent is dichloromethane, chloroform, dioxane, toluene, hexanes, heptane, methyl tert-butyl ether, diethyl ether, isopropanol, ethanol, methanol, ethyl acetate, isopropyl acetate, acetonitrile, water, or combinations thereof, or the like. In some embodiments, the suitable solvent is dioxane.

In some embodiments, the suitable acid is trifluoroacetic acid, hydrochloric acid, or phosphoric acid, or the like. In some embodiments, the suitable acid is trifluoroacetic acid. In some embodiments, the suitable acid is hydrochloric acid.

In some embodiments, the acid addition salt is a 2,2,2-trifluoroacetate salt. In some embodiments, the acid addition salt is the bis(2,2,2-trifluoroacetate) salt. In some embodiments, the acid addition salt is a hydrochloride salt. In some embodiments, the acid addition salt is the dihydrochloride salt.

In some embodiments, the acid addition salt is isolated. In other embodiments, the acid addition salt is taken to the next step without isolation.

Step 2: Preparing Free Base Compound 1

In some embodiments, the free base of Compound 1 is prepared by contacting an acid addition salt of Compound 1 with a suitable base in a suitable solvent.

In some embodiments, the suitable solvent is dichloromethane, chloroform, toluene, methyl tert-butyl ether, diethyl ether, ethyl acetate, water, or combinations thereof, or the like. In some embodiments, the suitable solvent is a combination of water and ethyl acetate.

In some embodiments, the suitable base is sodium hydroxide, lithium hydroxide, calcium hydroxide, sodium bicarbonate, potassium bicarbonate, or ammonium hydroxide, or the like. In some embodiments, the suitable base is sodium hydroxide. In some embodiments, the suitable base is sodium bicarbonate.

In some embodiments, the pH is adjusted to pH of greater than 8 with the suitable base. In some embodiments, the pH is adjusted to pH of from about 8 to about 10 with the suitable base. In some embodiments, the pH is adjusted to pH of from about 9 to about 10 with the suitable base. In some embodiments, the pH is adjusted to pH of from about 9.5 to about 10 with the suitable base. In some embodiments, the pH is adjusted to pH of about 9.5 with the suitable base. In some embodiments, the pH is adjusted to pH of about 9.6 with the suitable base. In some embodiments, the pH is adjusted to pH of about 9.7 with the suitable base. In some embodiments, the pH is adjusted to pH of about 9.8 with the suitable base. In some embodiments, the pH is adjusted to pH of about 9.9 with the suitable base. In some embodiments, the pH is adjusted to pH of about 10 with the suitable base.

In some embodiments, the isolated Compound 1 is further dried. In some embodiments, the isolated Compound 1 is dried under vacuum. In some embodiments, the isolated Compound 1 is dried under vacuum at an elevated temperature. In some embodiments, the isolated Compound 1 is dried under static vacuum at about 50° C.

In some embodiments, the isolated Compound 1 is crystalline Pattern A of Compound 1. In some embodiments, the isolated Compound 1 is crystalline Pattern A of Compound 1 which is substantially free from other solid-state forms, such as Patterns B, C, and D, and amorphous Compound 1.

In some embodiments, when the free basing step does not go to sufficiently high pH, additional solid-state forms can be isolated, such as Patterns B and/or D. In some embodiments, performing the free base step at sufficiently high pH provides crystalline Pattern A of Compound 1. In some embodiments, performing the free base step at sufficiently high pH provides crystalline Pattern A of Compound 1 substantially free from other solid-state forms, such as Patterns B, C, and D, and amorphous Compound 1.

Preparation of Crystalline Pattern A of Compound 1

In some embodiments, as described above, Crystalline Pattern A of Compound 1 is prepared directly following preparation of free base Compound 1 from the acid addition salt of Compound 1. In such embodiments, when the pH of the mixture is a sufficiently high pH, e.g., from about pH 9 to pH 10, crystalline Pattern A is obtained. In other embodiments, Compound 1 (amorphous, or contaminated with other crystalline Patterns) is converted to crystalline Pattern A.

In some embodiments, crystalline Pattern A of Compound 1 is prepared by forming a slurry in a suitable solvent and filtering the slurry. In some embodiments, the suitable solvent is water, isopropanol, tetrahydrofuran, heptane, diethyl ether, or a combination thereof. In some embodiments, the suitable solvent is a mixture of water and isopropanol. In some embodiments, the suitable solvent comprises from about 10% to about 50% water in isopropanol. In some embodiments, the suitable solvent comprises about 10% water, about 20% water, about 30% water, about 40% water, or about 50% water in isopropanol. In some embodiments, the suitable solvent comprises about 10% water in isopropanol. In other embodiments, the suitable solvent is a mixture of THF and heptane.

In some embodiments, crystalline Pattern A of Compound 1 is prepared by forming a slurry in a suitable solvent, adjusting the pH of the slurry with a suitable base, and then filtering the slurry. In some embodiments, the suitable solvent is water. In some embodiments, the suitable base is sodium hydroxide, lithium hydroxide, calcium hydroxide, sodium bicarbonate, potassium bicarbonate, or ammonium hydroxide, or the like. In some embodiments, the suitable base is sodium hydroxide. In some embodiments, the suitable base is sodium bicarbonate. In some embodiments, the pH is adjusted to pH of greater than 8 with the suitable base. In some embodiments, the pH is adjusted to pH of from about 8 to about 10 with the suitable base. In some embodiments, the pH is adjusted to pH of from about 9 to about 10 with the suitable base. In some embodiments, the pH is adjusted to pH of from about 9.5 to about 10 with the suitable base. In some embodiments, the pH is adjusted to pH of about 9.5 with the suitable base. In some embodiments, the pH is adjusted to pH of about 9.6 with the suitable base. In some embodiments, the pH is adjusted to pH of about 9.7 with the suitable base. In some embodiments, the pH is adjusted to pH of about 9.8 with the suitable base. In some embodiments, the pH is adjusted to pH of about 9.9 with the suitable base. In some embodiments, the pH is adjusted to pH of about 10 with the suitable base.

In some embodiments, crystalline Pattern A of Compound 1 is prepared by evaporative crystallization of Compound 1. In some embodiments, a slurry of Compound 1 is formed in a suitable solvent and solvent portion of the slurry is evaporated to provide crystalline Pattern A of Compound 1. In some embodiments, the solvent is evaporated to dryness at elevated temperature, e.g., 45° C. In some embodiments, the suitable solvent is diether either, water containing about 2.5% SDS, or a mixture of isopropanol and water.

In some embodiments, crystalline Pattern A of Compound 1 is prepared by antisolvent crystallization of Compound 1 with a suitable solvent mixture comprising a suitable solvent and a suitable antisolvent. In some embodiments, crystalline Pattern A of Compound 1 is prepared by direct antisolvent crystallization of Compound 1. In some embodiments, crystalline Pattern A of Compound 1 is prepared by reverse antisolvent crystallization of Compound 1. In some embodiments, the solvent used is isopropanol, tetrahydrofuran, or ethyl acetate. In some embodiments, the antisolvent used is water or heptane. In some embodiments, the solvent mixtures used are: isopropanol/water, tetrahydrofuran/water, tetrahydrofuran/heptane, ethyl acetate/heptane, or isopropanol/heptane.

In some embodiments, crystalline Pattern A of Compound 1 is prepared by cooling crystallization of Compound 1 in a suitable solvent. In some embodiments, the suitable solvent is isopropyl acetate, dichloromethane, isopropanol, water, tetrahydrofuran, heptane, ethyl acetate, methyl tert-butyl ether, acetonitrile, or a combination thereof. In some embodiments, the suitable solvent is: isopropyl acetate, dichloromethane, a mixture of isopropanol and water, a mixture of tetrahydrofuran and heptane, a mixture of ethyl acetate and methyl tert-butyl ether, or a mixture of acetonitrile and heptane.

In some embodiments, crystalline Pattern A of Compound 1 is prepared by vapor diffusion of anhydrous Compound 1. In some embodiments, the solvent used for vapor diffusion is water, isopropyl acetate, toluene, or dichloromethane.

In some embodiments, the isolated crystalline Pattern A of Compound 1 is further dried. In some embodiments, the isolated crystalline Pattern A of Compound 1 is dried under vacuum. In some embodiments, the isolated crystalline Pattern A of Compound 1 is dried under vacuum at an elevated temperature. In some embodiments, the isolated crystalline Pattern A of Compound 1 is dried under static vacuum at about 50° C.

In some embodiments, crystalline Pattern A of Compound 1 is dry. In some embodiments, crystalline Pattern A of Compound 1 is unsolvated. In some embodiments, crystalline Pattern A of Compound 1 is anhydrous.

In some embodiments, the crystalline Compound 1 is solvated. In some embodiments, the crystalline Compound 1 is hydrated. In some embodiments, crystalline Pattern A of Compound 1 is a monohydrate.

Certain Terminology

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCHNHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid. In some embodiments, a compound disclosed herein is prepared as a hydrochloride salt.

It should be understood that a reference to a crystalline forms herein includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "substantially the same," as used herein to reference a Fig. is intended to mean that the Fig. is considered representative of the type and kind of characteristic data that is obtained by a skilled artisan in view of deviations acceptable in the art. Such deviations may be caused by factors related to sample size, sample preparation, particular instrument used, operation conditions, and other experimental condition variations known in the art. For example, one skilled in the art can appreciate that the endotherm onset and peak temperatures as measured by differential scanning calorimetry (DSC) may vary significantly from experiment to experiment. For example, one skilled in the art can readily identify whether two X-ray diffraction patterns or two DSC thermograms are substantially the same. In some embodiments, when characteristic peaks of two X-ray diffraction patterns do not vary more than +0.2° 2-Theta, it is deemed that the X-ray diffraction patterns are substantially the same.

Pharmaceutical Compositions

In some embodiments, the compounds and solid state forms described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds and solid state forms described herein are administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, Compound 1, or a pharmaceutically acceptable salt thereof, is used in the preparation of medicaments for the treatment of diseases or conditions in a mammal that would benefit from modulation of SSTR5 activity. Methods for treating any of the diseases or conditions described herein in a mammal in need of such treatment, involves administration of pharmaceutical compositions that include Compound 1, or a pharmaceutically acceptable salt thereof, in therapeutically effective amounts to said mammal.

In some embodiments, Compound 1, or a pharmaceutically acceptable salt thereof, is amenable to oral administration to a mammal in need of treatment with a somatostatin modulator.

In some embodiments, Compound 1, or a pharmaceutically acceptable salt thereof, has utility over a wide range of therapeutic applications. In some embodiments, Compound 1, or a pharmaceutically acceptable salt thereof, is used in the treatment of a variety of diseases or conditions such as, but not limited to, acromegaly, neuroendocrine tumors and hyperinsulinism. In some embodiments, Compound 1, or a pharmaceutically acceptable salt thereof, is used in the treatment of hyperinsulinism in a mammal.

In some embodiments, Compound 1, or a pharmaceutically acceptable salt thereof, inhibits the secretion of various hormones and trophic factors in mammals. In some embodiments, Compound 1, or a pharmaceutically acceptable salt thereof, is used to suppress certain endocrine secretions, such as, but not limited to GH, IGF-1 and insulin. The suppression of certain endocrine secretions is useful in the treatment of disorders such as acromegaly, hyperinsulinism, endocrine tumors such as carcinoids, VIPomas, insulinomas and glucagonomas. In some embodiments, Compound 1, or a pharmaceutically acceptable salt thereof, is used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of Compound 1, or a pharmaceutically acceptable salt thereof, include cancers of the breast, prostate, and lung (both small cell and non-small cell epidermoids), as well as hepatomas, neuroblastomas, insulinomas, colon and pancreatic adenocarcinomas (ductal type), chondrosarcomas, and melanomas, and atherosclerosis associated with vascular grafts and restenosis following angioplasty.

In some embodiments, Compound 1, or a pharmaceutically acceptable salt thereof, is used to treat hyperinsulinemia in a mammal. Hyperinsulinemia leads to several conditions, such as but not limited to, hypoglycemia or low blood sugar, diabetes or uncontrolled blood sugar that fluctuates between a low and high level, increased risk of Polycystic Ovarian Syndrome (PCOS), increased production of very low-density lipoproteins (VLDLs) (referred to as hypertriglyceridemia), increased risk of cardiovascular or heart disease, coronary artery disease (the high insulin level damages the endothelial cells that line the coronary arteries), hypertension or high blood pressure, underactive thyroid gland, weight gain and lethargy.

Hyperinsulinism refers to an above normal level of insulin in the blood of a person or animal. Normal insulin secretion and blood levels are closely related to the level of glucose in the blood, so that a given level of insulin can be normal for one blood glucose level but low or high for another. Hyperinsulinism can be associated with several types of medical problems, which can be roughly divided into two broad and largely non-overlapping categories: those tending toward reduced sensitivity to insulin and high blood glucose levels (hyperglycemia), and those tending toward excessive insulin secretion and low glucose levels (hypoglycemia).

Hyperinsulinemic hypoglycemia (HH) is one of the most frequent causes of persistent hypoglycemia in infants. It is a heterogeneous condition caused by increased insulin secretion from pancreatic β-cells. HH can result in apneas, seizures, developmental delays, learning disabilities, epilepsy, and even death. The most severe form of HH is inherited and referred to as congenital hyperinsulinism (CHI). As with many rare diseases, there are no current drugs specifically tailored for patients with CHI, though some drugs have been adapted for use, including but not limited to diazoxide and octreotide.

The pancreas is a principal site of somatostatin action, and there it inhibits the synthesis and secretion of the two major hormones that control glucose homeostasis: glucagon and insulin. Different somatostatin receptor subtypes control these vital processes: SST2 receptors suppress glucagon, while both SSTR2 and SSTR5 are responsible for the suppression of insulin.

Hypoglycemia due to excessive endogenous insulin can be congenital or acquired, apparent in the newborn period, or many years later. The hypoglycemia can be severe and life-threatening or a minor, occasional nuisance. By far the most common type of severe but transient hyperinsulinemic hypoglycemia occurs accidentally in persons with type 1 diabetes who take insulin.

Hypoglycemia due to endogenous insulin includes, but is not limited to, congenital hyperinsulinism, transient neonatal hyperinsulinism, focal hyperinsulinism (KATP channel disorders), diffuse hyperinsulinism, acquired forms of hyperinsulinism, insulinomas (insulin-secreting tumors), adult nesidioblastosis, autoimmune insulin syndrome, non-insulinoma pancreatogenous hypoglycemia, reactive hypoglycemia, a side effect of gastric bypass surgery or gastric dumping syndrome.

Drug induced hyperinsulinism results from exposure to certain drugs such as, but not limited to, sulfonylureas, aspirin, pentamidine, quinine, disopyramide, *Bordetella pertussis* vaccine or infection, D-chiro-inositol and myo-inositol.

Hypoglycemia due to exogenous (injected) insulin includes but is not limited to, insulin self-injected for treatment of diabetes (i.e., diabetic hypoglycemia), insulin self-injected surreptitiously (e.g., Munchausen syndrome), insulin self-injected in a suicide attempt or successful suicide, insulin potentiation therapy, and insulin-induced coma for depression treatment.

In certain embodiments, the compositions containing the compounds and solid state forms described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-1000 mg per day. In one embodiment, the desired dose is conveniently presented in a single dose or in divided doses administered simultaneously or at appropriate intervals, for example as two, three, four or more sub-doses per day. In any of the aforementioned aspects are further embodiments in which the effective amount of Compound 1, or a pharmaceutically acceptable salt thereof, is: (a) systemically administered to the mammal; and/or (b) administered orally to the mammal. In some embodiments, the dose is administered once a day. In some embodiments, the dose is administered twice a day.

EXAMPLES

Abbreviations

ACN or MeCN=acetonitrile;
AcOH acetic acid;
Compound 4-[(3S)-3-aminopyrrolidin-1-yl]-6-cyano-5-(3,5-difluorophenyl)-N-[(2S)-1,1,1-trifluoropropan-2-yl]pyridine-3-carboxamide; or 4-((S)-3-aminopyrrolidin-1-yl)-6-cyano-5-(3,5-difluorophenyl)-N—((S)-1,1,1-trifluoropropan-2-yl)nicotinamide);
DCM=dichloromethane;
DI=deionized;
DMF=N,N-dimethylformamide;
DSC=differential scanning calorimetry;
DVS=dynamic vapor sorption;
EtOAc=ethyl acetate;
EtOH=ethanol;
Equiv. or eq. or Eq=equivalent(s);
FA=formic acid;
g=gram(s);
h or hr=hour;
HATU=(1-[Bis(dimethylamino)methylene]-1H-1,2,3-triazolo[4,5-b]-pyridinium 3-oxide hexafluorophosphate;
hrs=hours;
HPLC=high-performance liquid chromatography;
IPA=isopropyl alcohol; or isopropanol;
iPAc=isopropyl acetate;
kg or KG or Kg=kilogram(s);
L=liter;
M=molar;
MIBK=methyl isobutyl ketone;
MeOH=methanol;
mg=milligram(s);
mins or min=minutes;
mol.=mole;
mL or ml=milliliter;
μL=microliter;
mmol=millimole
MS=mass spectrometry;
MtBE=methyl tert-butyl ether;
NBS=N-bromosuccinimde;
NMR=nuclear magnetic resonance;
Pd(DtBPF)Cl$_2$=[1,1'-Bis(di-tert-butylphosphino)ferrocene]dichloropalladium(II);
Pd$_2$(dba)$_3$·CHCl$_3$=tris(dibenzylideneacetone)dipalladium (0)-chloroform adduct;
RH=relative humidity;
rpm=revolutions per minute;
rt or RT=room temperature;
s or sec=second(s);
SDS=sodium dodecyl sulfate;
t-BuOH=tert-butanoi;
TEA=triethyl amine;
TFA=trifluoroacetic acid:
TGA=thermogravimetric analysis;
THF=tetrahydrofuran;
vol or vols=volume(s);
w/w=weight ratio; and
XRPD=X-ray powder diffraction.

The following examples are provided for illustrative purposes only and not to limit the scope of the claims provided herein.

Example 1: Preparation of 4-[(3S)-3-aminopyrrolidin-1-yl]-6-cyano-5-(3,5-difluorophenyl)-N-[(2S)-1,1,1-trifluoropropan-2-yl]pyridine-3-carboxamide bis(2,2,2-trifluoroacetate) (Compound 1, 2×TFA Salt)

The preparation of Compound 1, TFA salt has been previously described (see, PCT/US2020/045610 and U.S. application Ser. No. 16/989,193, each of which is incorporated by reference in its entirety, each of which is incorporated by reference in its entirety).

Step 1, preparation of tert-butyl (S)-(1-(2-chloro-5-formylpyridin-4-yl)pyrrolidin-3-yl)carbamate: to a DMF (70 mL) solution was added 4,6-dichloronicotinaldehyde (6.8 g, 1.0 Eq, 39 mmol), tert-butyl (S)-pyrrolidin-3-ylcarbamate (7.6 g, 1.1 Eq, 41 mmol) and TEA (16 mL, 3.1 Eq, 120 mmol). The resulting mixture was stirred at 50° C. for 4 hours. The reaction crude was quenched with water (100 mL) and extracted with ethyl acetate (3×40 mL). The organic layers were combined, washed with brine, dried and concentrated under vacuum. The remaining residue was purified by silica gel chromatography eluting with ethyl acetate/petroleum ether (⅓) to afford tert-butyl (S)-(1-(2-chloro-5-formylpyridin-4-yl)pyrrolidin-3-yl)carbamate (5.3 g, 42%) as a yellow solid. MS (M+H)$^+$=326.2.

Step 2, preparation of tert-butyl(S)-(1-(3-bromo-2-chloro-5-formylpyridin-4-yl)pyrrolidin-3-yl)carbamate: to an AcOH (60 mL) solution of tert-butyl (S)-(1-(2-chloro-5-formylpyridin-4-yl)pyrrolidin-3-yl)carbamate (5.3 g, 1.0 Eq, 16 mmol) was added NBS (3.1 g, 1.1 Eq, 17 mmol) at 10° C. The resulting mixture was stirred at the same temperature for 1 hour. The reaction mixture was quenched with saturated NaHCO$_3$ and extracted with ethyl acetate (3×40 mL). The organic layers were combined, washed with brine, dried and concentrated under vacuum. The remaining residue was purified by silica gel chromatography eluting with ethyl acetate/petroleum ether (¼) to afford tert-butyl (S)-(1-(3-bromo-2-chloro-5-formylpyridin-4-yl)pyrrolidin-3-yl)carbamate (3.5 g, 53%) as a yellow solid. MS (M+H)$^+$=404.1, 406.1.

Step 3, preparation of tert-butyl(S)-(1-(2-chloro-3-(3,5-difluorophenyl)-5-formylpyridin-4-yl)pyrrolidin-3-yl)carbamate: to a mixture of tert-butyl (S)-(1-(3-bromo-2-chloro-5-formylpyridin-4-yl)pyrrolidin-3-yl)carbamate (3.5 g, 1.0 Eq, 8.6 mmol), (3,5-difluorophenyl)boronic acid (0.88 Eq, 7.6 mmol, 1.2 g), Pd(DtBPF)Cl$_2$ (300 mg, 0.05 Eq, 0.46 mmol) and potassium phosphate (5.4 g, 2.9 Eq, 25 mmol) was added toluene (140 mL) and water (14 mL) under atmospheric nitrogen. The resulting mixture was stirred at 40° C. for 2 hours. The reaction crude was concentrated under reduced pressure and the remaining residue was purified by silica gel column chromatography eluting with petroleum ether/EtOAc (3:1) to afford tert-butyl (S)-(1-(2-chloro-3-(3,5-difluorophenyl)-5-formylpyridin-4-yl)pyrrolidin-3-yl)carbamate (2.7 g, 71%) as a yellow solid. MS (M+H)$^+$=438.0, 440.0.

Step 4, preparation of tert-butyl (S)-(1-(2-cyano-3-(3,5-difluorophenyl)-5-formylpyridin-4-yl)pyrrolidin-3-yl)carbamate: to a mixture of tert-butyl (S)-(1-(2-chloro-3-(3,5-difluorophenyl)-5-formylpyridin-4-yl)pyrrolidin-3-yl)carbamate (2.7 g, 1.0 Eq, 6.2 mmol), Pd$_2$(dba)$_3$·CHCl$_3$ (310 mg, 0.05 Eq, 0.31 mmol), Zn(CN)$_2$ (1.4 g, 1.9 Eq, 12 mmol) and (9,9-dimethyl-9H-xanthene-4,5-diyl)bis(diphenylphosphane) (720 mg, 0.20 Eq, 1.24 mmol) was added DMF (30 mL) under atmospheric nitrogen. The resulting mixture was heated under microwave radiation conditions at 135° C. for 1 hour. The reaction crude was quenched with water (100 mL) and extracted with EtOAc (3×40 mL). Organic layers were combined, washed with brine, dried over anhydrous Na$_2$SO$_4$, filtered and concentrated under vacuum. The remaining residue was purified by silica gel chromatography eluting with petroleum ether/EtOAc (1:1) to afford tert-butyl (S)-(1-(2-cyano-3-(3,5-difluorophenyl)-5-formylpyridin-4-yl)pyrrolidin-3-yl)carbamate (2.2 g, 83%) as a yellow solid. MS (M+H)$^+$=429.2.

Step 5, preparation of (S)-4-(3-((tert-butoxycarbonyl)amino)pyrrolidin-1-yl)-6-cyano-5-(3,5-difluorophenyl)nicotinic acid: to a tert-butyl alcohol solution (20 mL) of (S)-(1-(2-cyano-3-(3,5-difluorophenyl)-5-formylpyridin-4-yl)pyrrolidin-3-yl)carbamate (2.4 g, 1.0 Eq, 5.1 mmol) was added sodium dihydrogen phosphate (2.4 g, 3.0 Eq, 15 mmol) 2-methylbut-2-ene (11.0 g, 31 Eq, 157 mmol), sodium chlorite (1.0 g, 2.2 Eq, 11 mmol) and water (6.6 mL). The resulting mixture was stirred at ambient temperature for 1 hour. The reaction mixture was quenched with saturated NaHSO$_4$ (50 mL) and extracted with ethyl acetate (3×40 mL). The organic layers were combined, washed with brine, dried and concentrated under vacuum to afford (S)-4-(3-((tert-butoxycarbonyl)amino)pyrrolidin-1-yl)-6-cyano-5-(3,5-difluorophenyl)nicotinic acid (2.0 g, 88%) as a yellow solid. This material was used for the next step without purification. MS (M+H)$^+$=445.2.

Step 6, preparation of tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (Compound 1a): to a DMF solution (2.0 mL) of (S)-4-(3-((tert-butoxycarbonyl)amino)pyrrolidin-1-yl)-6-cyano-5-(3,5-difluorophenyl) nicotinic acid (70 mg, 1.0 Eq, 0.16 mmol) was added (S)-1,1,1-trifluoropropan-2-amine hydrochloride (35 mg, 1.5 Eq, 0.23 mmol), N-ethyl-N-isopropylpropan-2-amine (4.4 Eq, 0.70 mmol, 0.12 mL) and HATU (60 mg, 1.0 Eq, 0.16 mmol). The resulting mixture was stirred at ambient temperature for 2 hours. The reaction crude was purified by Prep-HPLC using the following conditions: SunFire Prep C18 OBD Column, 19*150 mm 5 µm; mobile phase, Water (0.1% FA) and ACN (24.0% ACN up to 46.0% in 7 min); Total flow rate, 20 mL/min; Detector, UV 220 nm. This resulted in tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (45 mg, 53%) as a light yellow solid. MS (M+H)$^+$=540.3.

Step 7, preparation of 4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1): to a DCM solution (2.0 mL) of tert-butyl ((5)-1-(2-cyano-3-(3,5-difluorophenyl)-5-(((S)-1,1,1-trifluoropropan-2-yl)carbamoyl)pyridin-4-yl)pyrrolidin-3-yl)carbamate (45 mg, 1.0 Eq, 0.083 mmol) was added TFA (1.0 mL). The resulting mixture was stirred at ambient temperature for 2 hours. The reaction solution was concentrated and freeze-dried under vacuum to afford the 4-[(3S)-3-aminopyrrolidin-1-yl]-6-cyano-5-(3,5-difluorophenyl)-N-[(2S)-1,1,1-trifluoropropan-2-yl]pyridine-3-carboxamide bis(2,2,2-trifluoroacetate) (Compound 1, 2×TFA salt) (40.2 mg, 72%) as a light yellow solid. MS (M+H)$^+$=440.2.

Example 2: Preparation of 4-[(3S)-3-aminopyrrolidin-1-yl]-6-cyano-5-(3,5-difluorophenyl)-N-[(2S)-1,1,1-trifluoropropan-2-yl]pyridine-3-carboxamide dihydrochloride (Compound 1, 2×HCl salt)

A 50 mL flask was charged with tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (Compound 1a, Example 1, Step 6) (10.5 g, 1 Eq, 19.5 mmol). Hydrogen chloride in dioxane (4M) (200.0 mL, 40 Eq, 0.8 mol) was added and the mixture was stirred 2 hour at 25° C. The solution was concentrated under reduced pressure to afford the 4-[(3S)-3-aminopyrrolidin-1-yl]-6-cyano-5-(3,5-difluorophenyl)-N-[(2S)-1,1,1-trifluoropropan-2-yl]pyridine-3-carboxamide dihydrochloride (Compound 1, 2×HCl salt), as a solid, which is taken to the next step without purification.

Example 3: Preparation of 4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1, Free Base)

The solid 4-[(3S)-3-aminopyrrolidin-1-yl]-6-cyano-5-(3,5-difluorophenyl)-N-[(2S)-1,1,1-trifluoropropan-2-yl]pyridine-3-carboxamide dihydrochloride from Example 2 was diluted water (100 mL). The pH of the solution was adjusted to ~7-8 with saturated aqueous NaHCO$_3$, and the resulting solution was extracted with 3×40 mL of ethyl acetate. The organic layers were combined, washed with brine, dried and concentrated under vacuum. The crude product was further purified by Flash-Prep-HPLC to provide 4-[(3S)-3-amino-pyrrolidin-1-yl]-6-cyano-5-(3,5-difluorophenyl)-N-[(2S)-1,1,1-trifluoropropan-2-yl]pyridine-3-carboxamide (Compound 1) as a light yellow solid (7.32 g, 85.6% over two steps).

The same procedure is also used to convert the 2×TFA salt provided in Example 1 to the free base compound.

XRPD analysis of the obtained Compound 1 shows amorphous material. In some batches, the amorphous material shows trace Pattern A, trace Pattern B, or trace Pattern D.

Example 4: Preparation of Crystalline Pattern A of Compound 1

Compound 1 (314 mg, as prepared in Example 3) was weighed in a 4 mL vial and 1.5 mL (~5 vol.) of IPA:water (9:1) was added. The vial was vortexed and sonicated. A white slurry was obtained, and the vial was sealed with parafilm and left to stir (10 mm stir bar, 200 rpm) at room temperature. After 5 h, a thick, flowable white slurry formed. The slurry was filtered (filtered within 30 s, lab RH=9.0%). A sample of the wet cake was analyzed by XRPD confirming that the sample exhibited the high crystalline Pattern A.

The filtered wet solid was collected in a 4 mL vial and placed in a vacuum oven at 50° C. to dry overnight (static vacuum, 32 inHg). XRPD analysis of the dried solid showed Pattern A.

Example 5: Improved Preparation of Crystalline Pattern A of Compound 1

After it was determined that Patterns B, C and D were from a salt impurity in the originally used free base of Compound 1 (see Example 17), experiments were conducted to purify the free base using neat water and pH adjustment. Two samples were prepared using approximately 50 mg of a sample of Compound 1 free base contaminated with trace Pattern D (as prepared in Example 3) and 1 mL of distilled water for each sample. After vortexing and sonication, a flowable slurry was obtained. The pH of the first sample was adjusted from 6.42 to 9.71 using 0.2 molar solution of NaOH. No pH adjustment was done for the second sample.

XRPD analysis showed a pure freebase with crystalline Pattern A was obtained from the slurry prepared in neat water and pH-adjusted to ~pH 10, whereas Pattern A+D was obtained for the sample prepared in water without adjustment.

Example 6: Preparation of Amorphous Compound 1

Approximately 40 mg of Compound 1 (prepared in Example 3) was dissolved in either: (a) 15 vol. of ACN:water (8:2 vol.), (b) 12.5 vol. of t-BuOH, or (c) 35 vol. of t-BuOH:water (8:2 vol.) at room temperature and dipped in liquid nitrogen to freeze the solutions. The solid was transferred to a freeze dryer and kept overnight.

XRPD analysis on the solids generated by lyophilization confirmed amorphous patterns for all three samples.

Example 7: Preparation Crystalline Patterns B and C of Compound 1 from Amorphous Compound 1

Samples of amorphous Compound 1 (either 30 mg/mL or 60 mg/mL) were dissolved in DCM and were allowed to evaporate either at room temperature or 45° C. After stirring for about 40 min, the resulting slurries were filtered and analyzed by XRPD. Pattern B was obtained for the wet cakes of recovered solids. Pattern B changed to C after drying under static vacuum at 50° C. overnight.

In a separate experiment, about 71 mg of amorphous Compound 1 was weighed into a 4 mL vial and 10 vol. (710 µL) of DCM was added at room temperature. After stirring for 5 min, a thin slurry formed. XRPD analysis of a sample taken from the slurry after 1 h confirmed Pattern B. The vial was then transferred to a fridge at 5° C. for ~3 h and then to a freezer at −20° C. overnight. Small amount of solid settled to the bottom of the vial after cooling at −20° C., the yield was very low, about 6% w/w. XRPD confirmed Pattern B. Pattern B was left to dry on the benchtop at room temperature for 2 days. XRPD analysis on the sample after 2 days confirmed that Pattern B was stable. Thermal analysis on a small sample (0.7 mg) of Pattern B was performed by DSC.

Example 8: Preparation Crystalline Pattern D of Compound 1 from Amorphous Compound 1

A sample of 48.9 mg of amorphous Compound 1 and 3 vol. (~150 µL) of MIBK:heptane was prepared at 45° C. A small amount of gummy solid formed after addition of the solvent system. The vial was vortexed and sonicated few times to break the gum and a thin slurry was obtained after 5 min of stirring. The sample was left to stir at 45° C. for about 5 h and then transferred to a stir plate at room temperature. After stirring overnight at room temperature, the sample was filtered and the solid was collected for XRPD analysis. The yield was low, ~7% w/w.

XRPD analysis on the collected solid showed a new pattern, designated as Pattern D. Pattern D remained stable after drying on the benchtop at room temperature for 2 days. Thermal analysis on a small sample of Pattern D was performed by DSC.

Pattern D converted to C after overnight drying under active vacuum at room temperature.

Example 9: Polymorph Screen 1: Short-Term Slurries of Compound 1

Compound 1 (about 30 mg) was slurried in a selection of solvents and solvent systems (0.3-0.5 mL as appropriate to maintain adequate stirring) at either room temperature or 45° C. for 2 days. After stirring for two days, vials containing slurries were centrifuged and settled solids were recovered and filtered for XRPD analysis.

XRPD data from the room temperature samples from IPA:water (9:1 vol), IPA:water (7:3 vol), IPA:water (1:1 vol), THF:heptane (1:1 vol), water (2.5% SDS), and diethyl ether, and 45° C. samples from IPA:water (1:1 vol) and water (2.5% SDS) showed Pattern A. A new pattern, Pattern B, was obtained from the slurry in MIBK:heptane (1:1 vol) at 45° C. which converted to Pattern C after drying under vacuum at 50° C. Pattern A+trace B was obtained in DCM at room temperature and converted to Pattern A+trace C after drying under vacuum at 50° C.

Example 10: Polymorph Screen 2: Evaporative Crystallization of Compound 1

Compound 1 (about 30 mg) was slurried in a selection of solvents and solvent systems (0.3-0.5 mL as appropriate to maintain adequate stirring) at either room temperature or 45° C. for 2 days. After stirring for two days, vials containing slurries were centrifuged and the supernatant was recovered for evaporative crystallization.

The solutions were evaporated to dryness at 45° C. overnight in atmosphere without stirring and then placed at 50° C. under active vacuum (~32 inHg) for 3 h. When sufficient solids were obtained after evaporation and drying, they were analyzed by XRPD.

Solids obtained from IPA:water (9:1 vol), IPA:water (7:3 vol), IPA:water (1:1 vol), water (2.5% SDS), and diethyl ether were crystalline and showed Pattern A.

Solids obtained from IPAc, MtBE, EtOH:heptane (1:1 vol), toluene, ACN:heptane (1:1 vol), and MIBK:heptane (1:1 vol) were amorphous.

Example 11: Polymorph Screen 3: Antisolvent Crystallization of Compound 1

Compound 1 (about 25 mg) was dissolved in a solvent at room temperature. Antisolvent was added to the solutions using either direct or reverse addition method. Solvents used in the studies were IPA, THF, acetone, or ethyl acetate. Antisolvents used in the studies were water, heptane, or MtBE.

Direct Antisolvent Addition

For direct antisolvent addition, the initial volume of antisolvent added was twice the volume of the solvent. The antisolvent was added in four steps, dropwise, over one hour while stirring. Once solids were formed, the slurries were filtered, and the collected solids were analyzed by XRPD. If no slurries were formed, additional antisolvent, up to double the initial volume, was added in two steps over half an hour.

Only two experiments generated slurries that could be filtered, both with water as the antisolvent. The IPA/water and THF/water samples each provided crystalline solids showing Pattern A.

For samples prepared with heptane as antisolvent, a solution with a tacky solid that precipitated at the bottom of the vial was formed. The samples were left to stir at room temperature for 3 days and then moved to stir on a cold plate at 10° C. for one day. After this, solids precipitated and the samples were filtered and analyzed by XRPD. The THF/heptane and EtOAc/heptane samples each provided crystalline solids showing Pattern A.

None of the samples with MtBE as an antisolvent provided solids suitable for XRPD analysis.

Reverse Antisolvent Addition

A vial containing the antisolvent was prepared and set to stir at room temperature. The Compound 1 solution was then transferred all at once to the antisolvent vial. The volume of the antisolvent was four times the volume of the solvent. The slurries were filtered and sampled by XRPD.

As with the direct antisolvent addition, only IPA/water and THF/water produced slurries shortly after addition of the Compound 1 solution. Each sample provided crystalline solids showing Pattern A.

Experiments with heptane as antisolvent produced a two-layer slurry, where a thick layer formed on top of a thinner layer, directly after addition of the Compound 1 solution, and a tacky solid precipitated at the bottom of the vials. The two-layer slurry changed within two minutes of stirring to a solution with a tacky amber solid at the bottom of the vial. Vortexing and sonication did not break the tacky solid, and the solutions were left to stir at room temperature for 4 days. After 4 days, solids formed at the bottom of the vial and on the vial walls. The samples were filtered and showed Pattern A with an additional peak at 14.2° 2-Theta by XRPD.

None of the samples with MtBE as an antisolvent provided solids suitable for XRPD analysis.

Example 12: Polymorph Screen 5: Cooling Crystallization of Compound 1

Cooling crystallization experiments were completed using Crystalline Pattern A of Compound 1 as input material. For these experiments, about 17-23 mg of Crystalline Pattern A of Compound 1 was dissolved into a solvent or solvent mixture at 50° C. (35° C. for DCM) and was subjected to either fast cooling or slow cooling crystallization method.

Fast Cooling Crystallization

For fast-cooling experiments, the solutions at 50° C. were transferred to an ice-water bath at 0° C. without mixing and left undisturbed for 10 min. After 10 min, the ice-water bath containing the vials was moved to a stir plate. The solutions were left to stir at 400 rpm. After one hour of stirring at 0° C. no precipitation was observed, and all vials were moved to a freezer at −20° C. and left in the freezer for up to 5 days.

After cooling at −20° C., solids were collected from six of the eight samples and XRPD analysis confirmed Pattern A for all six samples (IPAc, DCM, IPA:water (1:1 vol), THF:heptane (1:1 vol), EtOAc:MtBE (1:1 vol), and ACN:heptane (4:6 vol).). Samples in MtBE and in EtOH:heptane (1:1 vol.) remained in solution and were not analyzed by XRPD.

Slow Cooling Crystallization

For slow-cooling experiments, solutions were prepared at 50° C. using 20-25 mg of crystalline Pattern A of Compound 1. The solutions were cooled from 50° C. to 25° C. at a controlled rate of 5° C./h with stirring. When precipitation occurred, samples were filtered and analyzed by XRPD.

Samples prepared in IPAc and in ACN:heptane (4:6 vol.) precipitated at 23° C. and were sampled by XRPD, confirming Pattern A.

The remaining samples were left to cool down to 4° C. at 5° C./h. Cooling was overnight and the samples were left at 4° C. for a few hours. After that time, samples in MtBE and in EtOH:heptane (4:6 vol.) remained in solutions whereas all other samples precipitated and confirmed to be Pattern A by XRPD (IPAc, DCM, IPA:water (1:1 vol), THF:heptane (1:1 vol), EtOAc:MtBE (1:1 vol), and ACN:heptane (4:6 vol)).

Example 13: Polymorph Screen 6: Milling of Compound 1

Dry and solvent drop milling was done using a small Wig-L-Bug ball mill with ¼" stainless steel ball as milling media. About 25 mg of crystalline Pattern A of Compound 1 was weighed into a milling capsule and one volume of solvent (solvent drop) was added. The milling was carried out at 3,800 rpm in three steps of 30 s each. The solids were recovered after milling and analyzed by XRPD.

Crystallinity of Pattern A was lost after dry milling resulting in amorphous material. Crystallinity of Pattern A remained stable after solvent milling in IPAc, water, and MIBK.

Example 14: Polymorph Screen 7: Vapor Diffusion of Compound 1

Vapor diffusion was performed using amorphous material generated in ACN:water (8:2 vol.) by lyophilization. About 15 mg of amorphous Compound 1 was weighed into 4 mL vials and placed, uncapped, inside 20 mL scintillation vials, each containing about 2 mL of water, heptane, MtBE, IPAc, toluene, DCM, dioxane, and MIBK.

After about 3 h, the MtBE and IPAc samples showed solutions with a small amount of gum lining the bottom of the vials. A ring of solution containing a small amount of solid was observed in DCM, and mostly dissolved solid was observed in dioxane. Glassy solids were observed in MIBK.

Solids collected from water, IPAc, toluene, and DCM were sampled by XRPD, confirming Pattern A. Solids were collected from the sample in MIBK after one week and XRPD analysis confirmed Pattern B. After 13 days, Pattern A was obtained for the sample in water and amorphous patterns were obtained for samples in heptane and MtBE.

Example 15: Thermal Stability of Crystalline Pattern A of Compound 1

Two samples of Crystalline Pattern A were prepared and cycled in the DSC and then analyzed by XRPD.

The first sample of Pattern A (9.4 mg) was heated from 30° C. to 150° C. and then cooled back to 30° C. The sample recovered from the DSC pan after the thermal cycling was a glassy, amber solid that did not look decomposed. XRPD analysis on this sample showed an amorphous pattern.

The second sample of Pattern A (14.4 mg) was heated from 30° C. to 118° C. and then cooled back to 30° C. The sample recovered after the DSC experiment appeared as a light-amber pellet that was easily pressed into a powder on the XRPD plate. XRPD analysis confirmed Pattern A was stable after the DSC treatment.

Example 16: Thermodynamic Stability of Crystalline Pattern A of Compound 1

One-week slurry stability studies were performed on crystalline Pattern A in five solvents and solvent systems at room temperature (20-24° C.) and at 10° C. About 25 mg of Compound 1 was weighed into 2 mL vials and the solvent was added to each vial at room temperature with stirring. The solvents and solvent systems used in the experiments were: IPA:water (1:1 vol), THF:heptane (1:2 vol), ACN:heptane (1:2 vol), MIBK:heptane (1:2 vol), and IPAc.

For the IPA:water (1:1 vol) samples, 10 vol. of IPA:water (1:1 vol) was added, whereas 7 vol. were initially added for the other solvent systems. One set of vials was left to stir at room temperature and the other set was transferred to a cold stir plate at 10° C. After 5 days, samples that remained in solutions were seeded with Pattern A (0.5-1 mg) and left to stir for one week.

Samples in ACN:heptane (1:2 vol) remained in solutions after one week of stirring at room temperature and at 10° C., so were unable to be analyzed by XRPD.

Pattern B was obtained for the sample in MIBK:heptane (1:2 vol) at 10° C.

Pattern A+trace of a new pattern, Pattern D, was obtained for the sample in MIBK:heptane (1:2 vol) at room temperature.

Pattern A was obtained for the remaining six samples that were able to be analyzed by XRPD.

Example 17: Nuclear Magnetic Resonance (NMR)

Proton NMR was performed on a Bruker Avance 300 MHz spectrometer. Solids were dissolved in 0.75 mL deuterated solvent (DMSO-$d_6$) in a 4 mL vial, transferred to an NMR tube (Wilmad 5 mm thin wall 8" 200 MHz, 506-PP-8) and analyzed according to the following parameters:

| Parameters - Bruker Avance 300 | |
| --- | --- |
| Instrument | Bruker Avance 300 MHz spectrometer |
| Temperature | 300 K |
| Probe | 5 mm PABBO BB-1H/DZ-GRD Z104275/0170 |
| Number of scans | 32 or 64 |
| Relaxation delay | 1.000 s |
| Pulse width | 14.2500 μs |
| Acquisition time | 2.9999 s |
| Spectrometer frequency | 300.15 Hz |
| Nucleus | $^1$H |

Analysis of the $^1$H NMR spectrum generated with samples of the amorphous material, Pattern A, Pattern B, Pattern C, and Pattern D showed that peaks in the aliphatic region were shifted downfield for patterns B, C and D as compared to the other samples. The shifts indicated that Patterns B, C, and D were related to a salt or excess acid present in the amorphous freebase materials.

Example 18. X-Ray Powder Diffraction (XRPD)

Although the following diffractometer was used, other types of diffractometers could be used. Furthermore, other wavelengths could be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2° 2-Theta.

XRPD was performed using a Bruker D8 Advance equipped with LYNXEYE detector in reflection mode (i.e. Bragg-Brentano geometry). Samples were prepared on Si zero-return wafers. The parameters for XRPD methods used are listed below:

| Parameter | Regular Scan | High Resolution Scan |
| --- | --- | --- |
| X-ray wavelength | Cu Kα1, 1.540598 Å | Cu Kα1, 1.540598 Å |
| X-ray tube setting | 40 kV, 40 mA | 40 kV, 40 mA |
| Slit condition | 0.6 mm div. + 2.5° soller | 0.6 mm div. + 2.5° soller |
| Scan mode | Step | Step |
| Scan range (°2θ) | 4-30 | 4-40 |
| Step size (°2θ) | 0.03 | 0.02 |
| Dwell time (s/step) | 0.23 | 0.9 |
| Spin | Yes (0.5 Hz) | Yes (0.5 Hz) |

Characterization of Solid State Forms and Patterns of Compound 1

The X-Ray powder diffraction pattern for amorphous Compound 1 shows a lack of crystallinity. The X-Ray powder diffraction pattern for crystalline Pattern A of Compound 1 is displayed in FIG. 1. The X-Ray powder diffraction pattern for crystalline Pattern B of Compound 1 is displayed in FIG. 5. The X-Ray powder diffraction pattern for crystalline Pattern C of Compound 1 is displayed in FIG.

Figure 13:
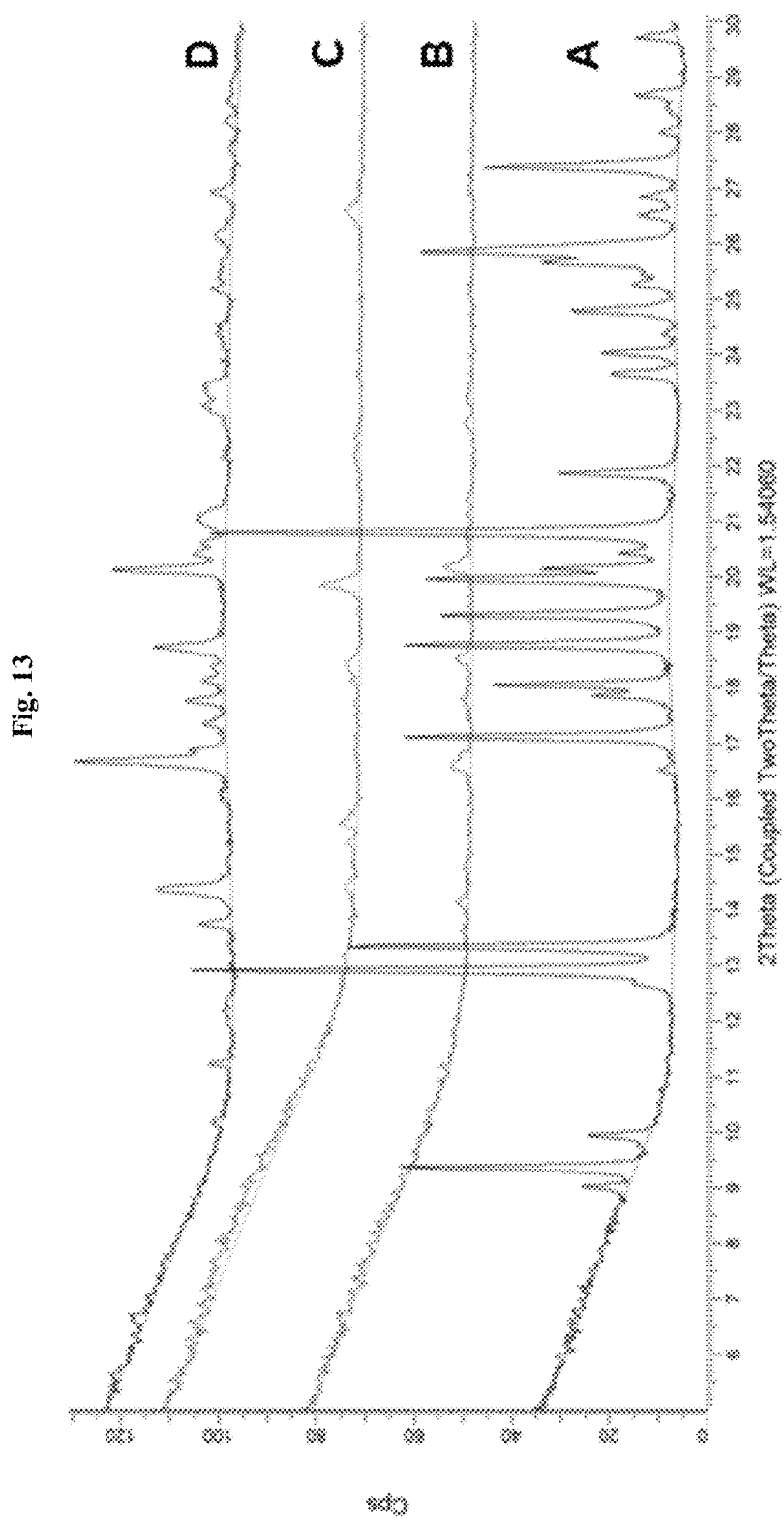
FIG. 13 illustrates an overlay of representative XRPD patterns for crystalline Patterns A, B, C, and D of Compound 1 as measured with Cu Kα1 radiation.

7. The X-Ray powder diffraction pattern for crystalline Pattern D of Compound 1 is displayed in FIG. 8. An overlay of the X-Ray powder diffraction patterns for crystalline Patterns A, B, C, and D of Compound 1 is displayed in FIG. 13.

Characterization of Crystalline Pattern A of Compound 1

The X-Ray powder diffraction pattern for crystalline Pattern A of Compound 1 is displayed in FIG. 1. Characteristic peaks include the peaks listed in the following table:

| Angle 2-Theta (°) | Rel. Intensity (%) |
|---|---|
| 9.4 | 42 |
| 12.9 | 90 |
| 13.3 | 64 |
| 17.1 | 55 |
| 18.7 | 53 |
| 19.3 | 48 |
| 20.7 | 100 |
| 25.8 | 57 |
| 27.3 | 46 |

Example 19: Differential Scanning Calorimetry (DSC)

DSC was performed using a Mettler Toledo DSC3+. The sample (1-3 mg) was weighed directly in a 40 μL hermetic aluminum pan with pin-hole and analyzed according to the parameters below:

| Parameters | |
|---|---|
| Method | Ramp |
| Sample size | 1-3 mg |
| Heating rate | 10.0° C./min |
| Temperature range | 30 to 350° C. |
| Method gas | N$_2$ at 60.00 mL/min |

The standalone DSC thermogram for crystalline Pattern A of Compound 1 is displayed in FIG. 2 and FIG. 3. The standalone DSC thermogram for crystalline Pattern B of Compound 1 is displayed in FIG. 6. The standalone DSC thermogram for crystalline Pattern D of Compound 1 is displayed in FIG. 9.

Differential Scanning calorimetry (DSC) thermogram endotherms for selected patterns are as described in the following table:

| Solid State Form | DSC Endotherms |
|---|---|
| Pattern A | endotherm with onset at 96.5° C. and peak at about 106.0° C.; or endotherm with onset at 86.6° C. and peak at about 101.4° C. |
| Pattern B | five broad endothermic events: onset at about 46.4° C. and peak at about 75.4° C.; onset at about 160.0° C. and peak at about 177.1° C.; onset at about 191.4° C. and peak at about 198.3° C.; onset at about 238.6° C. and peak at about 256.2° C.; and onset at about 259.1° C. and peak at about 292.0° C. |
| Pattern D | three broad endothermic events: onset at about 47.4° C. and peak at about 72.2° C.; onset at about 235.1° C. and peak at about 255.3° C.; and onset at about 265.5° C. and peak at about 278.8° C. |

Example 20: Simultaneous Thermogravimetric Analysis and Differential Scanning Calorimetry (TGA and DSC)

Thermogravimetric analysis and differential scanning calorimetry were performed on the same sample simultaneously using a Mettler Toledo TGA/DSC3+. Protective and purge gas was nitrogen at flowrate 20-30 mL/min and 50-100 mL/min, respectively. The desired amount of sample (5-10 mg) was weighed directly in a hermetic aluminum pan with pin-hole and analyzed according to the parameters below:

| Parameters | |
|---|---|
| Method | Ramp |
| Sample size | 5-10 mg |
| Heating rate | 10.0° C./min |
| Temperature range | 30-350° C. |

The simultaneous TGA and DSC patterns for amorphous Compound 1 is displayed in FIG. 11. A 1.2% w/w loss from 25 to 190° C. was observed for amorphous Compound 1 in the TGA pattern. The TGA pattern for crystalline Pattern A of Compound 1 is displayed in FIG. 3. A 3.08% w/w loss from 50 to 145° C. was observed for crystalline Pattern A of Compound 1 in the TGA pattern.

Example 21: Dynamic Vapor Sorption (DVS)

Dynamic Vapor Sorption (DVS) was performed using a DVS Intrinsic 1. The sample (10-15 mg) was loaded into a sample pan, suspended from a microbalance and exposed to a humidified stream of nitrogen gas. The sample was held for a minimum of 5 min at each level and only progressed to the next humidity level if there was <0.002% change in weight between measurements (interval: 60 seconds) or 240 min had elapsed. The following program was used:

(1) Equilibration at 50% RH
(2) 50% to 2% (50%, 40%, 30%, 20%, 10% and 2%)
(3) 2% to 95% (2%, 10%, 20%, 30%, 40%, 50%, 60%, 70%, 80%, 90%, 95%)
(4) 95% to 2% (95%, 80%, 70%, 60%, 50%, 40%, 30%, 20%, 10%, 2%)
(5) 2% to 50% (2%, 10%, 20%, 30%, 40%, 50%)

DVS analysis of Pattern A showed that the total mass change between 2 and 95% RH was 0.7%. The mass loss from 50 to 2% RH was 0.2% and the mass gain from 20 to 75% RH was 0.37%. XRPD analysis on the sample measured by DVS confirmed a stable Pattern A (unchanged after DVS analysis).

Example 22: Stability of Solid State Forms on Humidity Exposure

Samples were assessed for stability under static storage conditions of 40° C./75% RH for 7 days. The samples were then re-analyzed by XRPD.

There was no change in the XRPD of crystalline Pattern A.

Example 23: High-Performance Liquid Chromatography (HPLC) Methods

Agilent 1220 Infinity LC

High performance liquid chromatography (HPLC) was conducted using an Agilent 1220 Infinity LC. Flow rate range was 0.2-5.0 mL/min, operating pressure range was 0-600 bar, temperature range was 5° C. above ambient to 60° C., and wavelength range was 190-600 nm.

Agilent 1220 Infinity 2 LC

High performance liquid chromatography (HPLC) was conducted using an Agilent 1220 Infinity 2 LC equipped with diode array detector (DAD). Flow rate range is 0.2-5.0 mL/min, operating pressure range is 0-600 bar, temperature range is 5° C. above ambient to 60° C., and wavelength range is 190-600 nm.

The HPLC method used is shown below:

| Parameter | Value | | |
|---|---|---|---|
| Mobile phase A | 0.05% TFA in distilled water | | |
| Mobile phase B | 0.05% TFA in CAN | | |
| Diluent | ACN:water (1:1 vol) | | |
| Injection volume | 5 μL | | |
| Monitoring wavelength | 210 nm | | |
| Column | Halo C-18, 4.6 × 150 mm, 3.5 μm | | |
| Flow rate | 1.00 mL/min | | |
| | Time (min) | % Phase A | % Phase B |
| Gradient Method | 0 | 95 | 5 |
| | 0.1 | 95 | 5 |
| | 3 | 95 | 5 |
| | 18 | 5 | 95 |
| | 20 | 5 | 95 |
| | 20.1 | 95 | 5 |
| | 25 | 95 | 5 |

Purity analysis of the different solid-state forms indicated >98% purity of all forms and patterns.

Example 24: Single Crystal X-Ray Diffraction (SCXRD)

Preparation of Single Crystal

Crystals of good quality for single crystal structure determination of Crystalline Pattern A of Compound 1 were obtained through vapor diffusion of ethanol and hexane. The approximate dimensions of the crystal were: 0.295×0.230× 0.135 mm³, cut into shape with a razor blade. The crystal was mounted on a MiTeGen™ mount with mineral oil (STP Oil Treatment) and first diffraction patterns showed the crystal to be of excellent quality without signs of non-merohedral twinning.

Data Collection and Data Reduction

Diffraction data (φ- and ω-scans) were collected at 100K on a Bruker-AXS X8 Kappa diffractometer coupled to a Bruker Photon2 CPAD detector using Cu Kα radiation ($\lambda$=1.54178 Å) from an IμS microsource. Data reduction was carried out with the program SAINT and semi-empirical absorption correction based on equivalents was performed with the program SADABS. A summary of crystal properties and data/refinement statistics is given in Table 1, below.

Structure Solution and Refinement

The structure was solved with dual-space methods using the program SHELXT and refined against F2 on all data with SHELXL using established refinement techniques. All non-hydrogen atoms were refined anisotropically. All carbon-bound hydrogen atoms were placed in geometrically calculated positions and refined using a riding model while constraining their Uiso to 1.2 times the Ueq of the atoms to which they bind (1.5 times for the $CH_3$ group). Coordinates for the hydrogen atoms connected to nitrogen and oxygen were taken from the difference Fourier synthesis and those hydrogen atoms were subsequently refined semi-freely with the help of distance restraints on the O—H and N—H distances (target values 0.84(2) Å for OH, 0.88(2) Å for amid NH, and 0.91(2) Å for amine NH). No other restraints were applied.

TABLE 1

Data collection and structure refinement for Compound 1, Pattern A

| | |
|---|---|
| Temperature | 100(2) K |
| Wavelength | 1.54178 Å |
| Crystal system | Monoclinic |
| Space group | $P2_1$ |
| Unit cell dimensions | a = 10.1810(2) Å α = 90° |
| | b = 9.9510(2) Å β = 114.6748(5)° |
| | c = 10.7342(2) Å γ = 90° |
| Volume | 988.20(3) Å³ |
| Z | 2 |
| Density (calculated) | 1.537 Mg/m³ |
| Absorption coefficient | 1.169 mm⁻¹ |
| F(000) | 472 |
| Crystal size | 0.295 × 0.230 × 0.135 mm³ |
| Theta range for data collection | 4.533 to 74.519° |
| Index ranges | −12 ≤ h ≤ 12, −12 ≤ k ≤ 12, −13 ≤ l ≤ 12 |
| Reflections collected | 38889 |
| Independent reflections | 4044 [$R_{int}$ = 0.0267] |
| Completeness to theta = 67.679° | 99.9% |
| Absorption correction | Semi-empirical from equivalents |
| Refinement method | Full-matrix least-squares on F² |
| Data/restraints/parameters | 4044/6/305 |
| Goodness-to-fit on F² | 1.078 |
| Final R indices [I > 2σ(I)] | R1 = 0.0220, wR2 = 0.0579 |
| R indices (all data) | R1 = 0.0220, wR2 = 0.0579 |
| Absolute structure parameter | 0.047(12) |
| Largest diff. peak and hole | 0.221 and −0.173 e · Å⁻³ |

Crystal Structure

The crystal structure of Compound 1 monohydrate, Pattern A was determined at 100 K and a summary of the structural data can be found in Tables 2, 3, 4, and 5.

Figure 14:
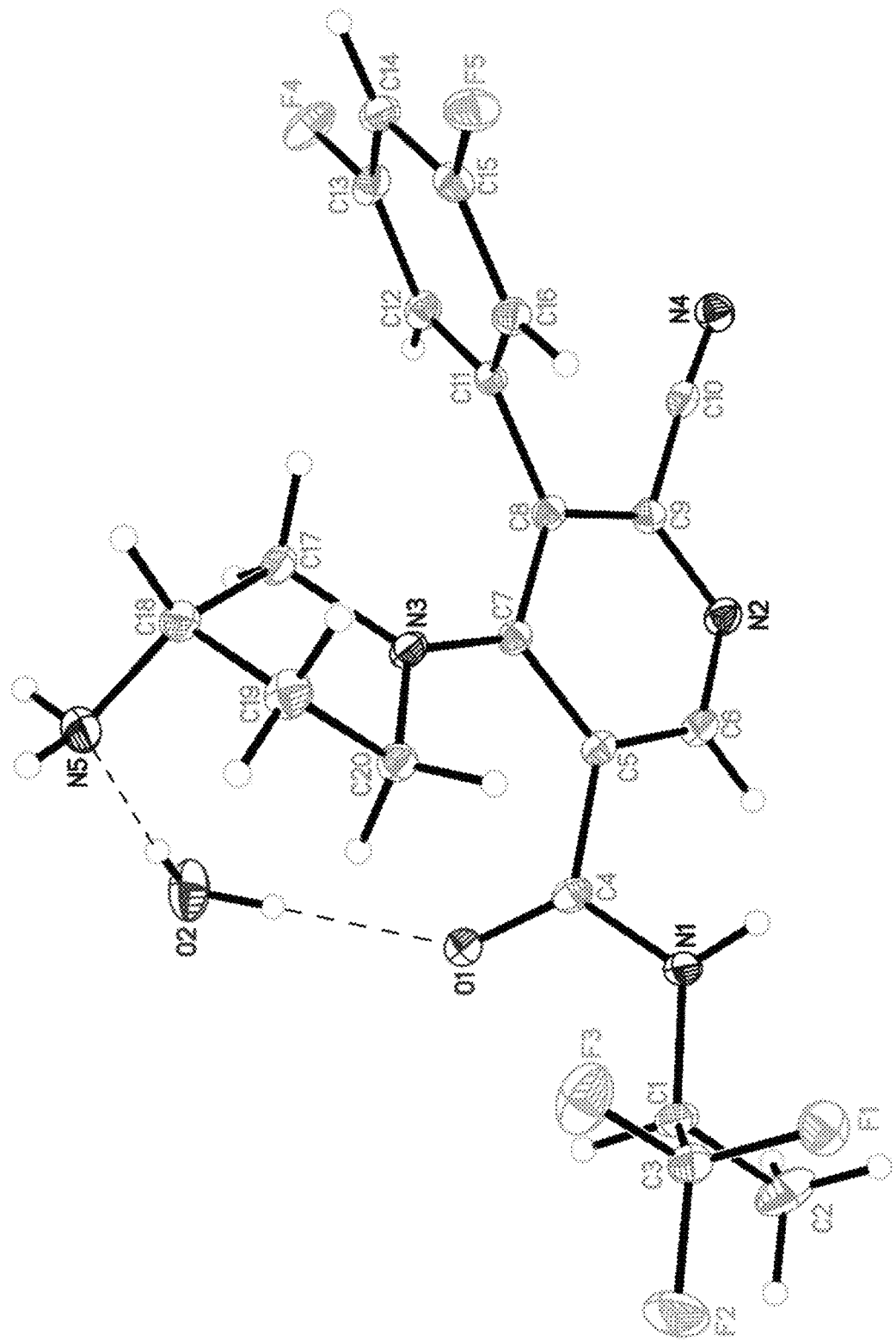
FIG. 14 depicts a thermal ellipsoid representation of all atoms in the asymmetric unit of Compound 1 monohydrate.

Compound 1 monohydrate crystallizes in the monoclinic chiral space group $P2_1$ with one molecule of Compound 1, and on molecule of water in the asymmetric unit. FIG. 14 depicts a thermal ellipsoid representation of all atoms in the asymmetric unit Compound 1 monohydrate at the 50% probability level. In this representation, the hydrogen bonds are drawn as thin dashed lines. The structure has five classical and six non-classical hydrogen bonds. Hydrogen bonds O2-H2A . . . N5 and O2-H2B . . . O1 link the water to the main molecule. The water is further connected to the Compound 1 molecule by the classical interaction N5-HSA . . . O2$^i$ (symmetry operator i: −x+2, y−½, −z+1), which links the molecules into infinite helical chains extending along the crystallographic b-axis. Those chains are crosslinked to infinite sheets extending parallel to the crystallographic a-b-plane by the N1-H1 . . . N4$^{ii}$ hydrogen bond as well as the non-classical C6-H6 . . . F5$^{iii}$ C12-H12 . . . O2$^{iv}$, and C16-H16 . . . N2$^{ii}$ interactions (symmetry operators ii: −x+1, y+½, −z+1; −x+1; y−½, −z+1; iv: −x+2, y+½, −z+1). Finally, hydrogen bond N5-H5B . . . F2$^v$ (symmetry operator v: x, y, z−1) connects the sheets in the third dimension (the crystallographic c-direction), giving rise to the supramolecular arrangement.

TABLE 2

Crystal Data of Compound 1 monohydrate, Pattern A at 100 K

| | |
|---|---|
| Crystal System | Monoclinic |
| Space Group | P2$_1$ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å$^3$) | 988.20(3) |
| Z | 2 |
| Calculated Density (Mg/m$^3$) | 1.537 |
| Absorption coefficient (mm$^{-1}$) | 1.169 |
| F(000) | 472 |

TABLE 3

Atomic Coordinates and equivalent isotropic displacement parameters for Compound 1 monohydrate, Pattern A at 100 K

| | x [×10$^4$] | y [×10$^4$] | z [×10$^4$] | U(eq) [Å$^2$ × 10$^3$] |
|---|---|---|---|---|
| F(1) | 7129(1) | 3020(1) | 10434(1) | 22(1) |
| F(2) | 9216(1) | 2126(1) | 11573(1) | 33(1) |
| F(3) | 8141(1) | 1866(1) | 9378(1) | 32(1) |
| F(4) | 5567(1) | 6144(1) | −636(1) | 23(1) |
| F(5) | 2546(1) | 3373(1) | 559(1) | 20(1) |
| O(1) | 9824(1) | 4111(1) | 7950(1) | 18(1) |
| N(1) | 8242(1) | 4590(1) | 8875(1) | 14(1) |
| N(2) | 6807(2) | 7569(1) | 5810(1) | 16(1) |
| N(3) | 7367(1) | 3501(1) | 4949(1) | 14(1) |
| N(4) | 4962(2) | 8897(1) | 2700(1) | 18(1) |
| N(5) | 9283(2) | 1135(2) | 4524(2) | 21(1) |
| C(1) | 9135(2) | 4012(2) | 10197(2) | 17(1) |
| C(2) | 9444(2) | 4996(2) | 11376(2) | 27(1) |
| C(3) | 8398(2) | 2755(2) | 10391(2) | 19(1) |
| C(4) | 8665(2) | 4584(2) | 7835(2) | 14(1) |
| C(5) | 7676(2) | 5319(2) | 6572(2) | 13(1) |
| C(6) | 7431(2) | 6656(2) | 6791(2) | 16(1) |
| C(7) | 7185(2) | 4811(2) | 5213(2) | 12(1) |
| C(8) | 6433(2) | 5760(2) | 4150(2) | 12(1) |
| C(9) | 6340(2) | 7085(2) | 4529(2) | 13(1) |
| C(10) | 5584(2) | 8083(2) | 3478(2) | 14(1) |
| C(11) | 5616(2) | 5400(2) | 2676(2) | 12(1) |

TABLE 3-continued

Atomic Coordinates and equivalent isotropic displacement parameters for Compound 1 monohydrate, Pattern A at 100 K

| | x [×10$^4$] | y [×10$^4$] | z [×10$^4$] | U(eq) [Å$^2$ × 10$^3$] |
|---|---|---|---|---|
| C(12) | 5996(2) | 5958(2) | 1680(2) | 15(1) |
| C(13) | 5187(2) | 5599(2) | 325(2) | 16(1) |
| C(14) | 4037(2) | 4718(2) | −94(2) | 16(1) |
| C(15) | 3684(2) | 4217(2) | 930(2) | 15(1) |
| C(16) | 4429(2) | 4534(2) | 2301(2) | 14(1) |
| C(17) | 7514(2) | 3005(2) | 3710(2) | 18(1) |
| C(18) | 7731(2) | 1484(2) | 3928(2) | 17(1) |
| C(19) | 7087(2) | 1178(2) | 4953(2) | 19(1) |
| C(20) | 7566(2) | 2385(2) | 5912(2) | 14(1) |
| O(2) | 11268(1) | 3062(2) | 6411(2) | 28(1) |

U(eq) is defined as one third of the trace of the orthogonalized U$^{ij}$ tensor.

TABLE 4

Hydrogen Coordinates and equivalent isotropic displacement parameters for Compound 1 monohydrate, Pattern A at 100 K

| | X [×10$^4$] | y [×10$^4$] | z [×10$^4$] | U(eq) [Å$^2$ × 10$^3$] |
|---|---|---|---|---|
| H(1) | 7340(20) | 4810(20) | 8690(20) | 17 |
| H(5A) | 9310(30) | 250(30) | 4670(30) | 31 |
| H(5B) | 9660(30) | 1320(30) | 3950(20) | 31 |
| H(1A) | 10079 | 3743 | 10191 | 20 |
| H(2C) | 9919 | 5799 | 11227 | 41 |
| H(2D) | 10079 | 4569 | 12241 | 41 |
| H(2E) | 8534 | 5254 | 11416 | 41 |
| H(6) | 7733 | 6942 | 7714 | 19 |
| H(12) | 6784 | 6566 | 1922 | 18 |
| H(14) | 3519 | 4469 | −1028 | 19 |
| H(16) | 4145 | 4174 | 2971 | 17 |
| H(17A) | 8355 | 3425 | 3627 | 22 |
| H(17B) | 6633 | 3205 | 2872 | 22 |
| H(18) | 7198 | 990 | 3048 | 20 |
| H(19A) | 6020 | 1115 | 4491 | 22 |
| H(19B) | 7480 | 330 | 5453 | 22 |
| H(20A) | 6953 | 2500 | 6418 | 17 |
| H(20B) | 8590 | 2302 | 6577 | 17 |
| H(2A) | 10710(30) | 2450(30) | 5900(30) | 41 |
| H(2B) | 10820(30) | 3390(30) | 6880(30) | 41 |

U(eq) is defined as one third of the trace of the orthogonalized U$^{ij}$ tensor.

TABLE 5

Hydrogen bonds for Compound 1 monohydrate, Pattern A at 100 K

| D-H . . . A | d(D-H) [Å] | d(H . . . A) [Å] | d(D . . . A) [Å] | <(DHA) [°] |
|---|---|---|---|---|
| N(1)—H(1) . . . N(4)#1 | 0.888(18) | 2.37(2) | 3.0615(19) | 134.9(18) |
| N(5)—H(5A) . . . O(2)#2 | 0.89(3) | 2.43(3) | 3.195(2) | 145(2) |
| N(5)—H(5B) . . . F(2)#3 | 0.88(2) | 2.53(2) | 3.2921(18) | 146(2) |
| C(1)—H(1A) . . . F(5)#4 | 1.00 | 2.40 | 3.3890(18) | 168.9 |
| C(2)—H(2C) . . . F(3)#5 | 0.98 | 2.55 | 3.438(2) | 150 |
| C(6)—H(6) . . . F(5)#6 | 0.95 | 2.45 | 3.3095(18) | 151 |
| C(12)—H(12) . . . O(2)#7 | 0.95 | 2.53 | 3.402(2) | 153.2 |
| C(16)—H(16) . . . N(2)#1 | 0.95 | 2.50 | 3.413(2) | 160.6 |
| C(20)—H(20B) . . . O(1) | 0.99 | 2.33 | 2.9696(19) | 121.2 |
| O(2)—H(2A) . . . N(5) | 0.86(2) | 2.05(2) | 2.906(2) | 174(3) |
| O(2)—H(2B) . . . O(1) | 0.87(2) | 1.96(2) | 2.8298(17) | 179(3) |

Symmetry transformations used to generate equivalent atoms:
1 −x + 1, y − 1/2, −z + 1
2 −x + 2, y − 1/2, −z + 1
3 x, y, z − 1
4 x + 1, y, z + 1
5 −x + 2, y + 1/2, −z + 2
6 −x + 1, y + 1/2, −z + 1
7 −x + 2, y + 1/2, −z + 1

Figure 15:
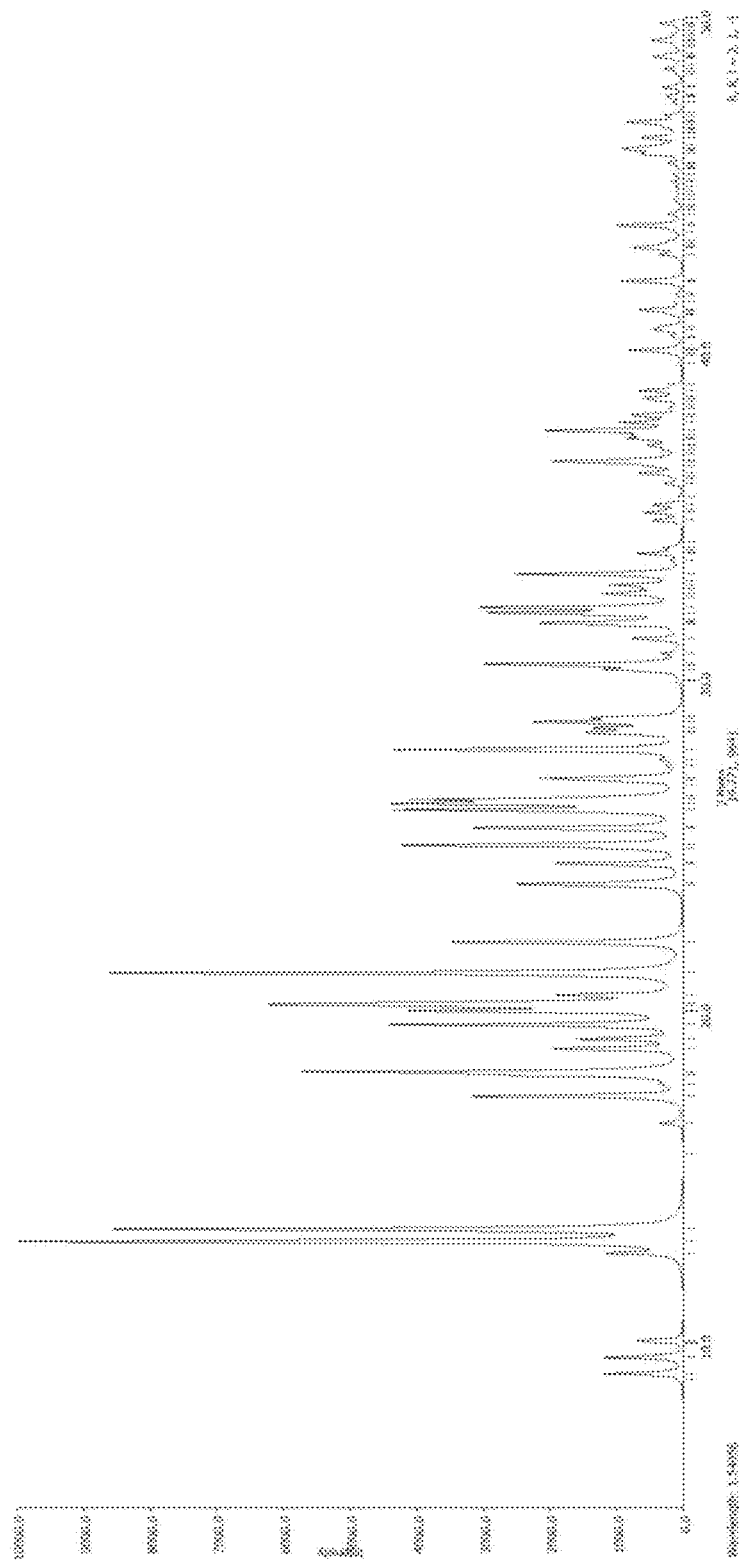
FIG. 15 depicts the simulated powder diffractogram for the crystal structure of Compound 1 monohydrate.

The simulated powder diffractogram for the crystal structure of Compound 1 monohydrate is shown in FIG. 15.

Figure 16:
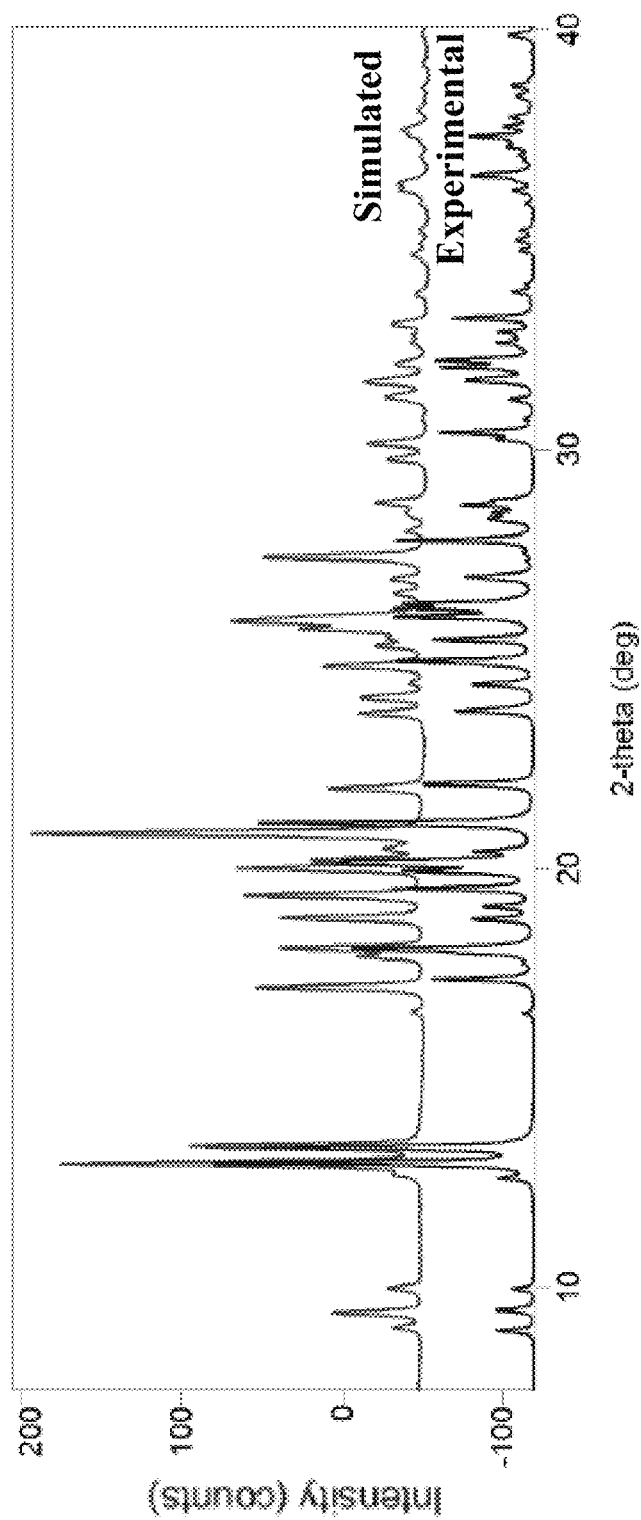
FIG. 16 depicts an overlay of the simulated diffractogram (top) with the experimental diffractogram (bottom) at room temperature.

An overlay of the simulated diffractogram (top) with the experimental diffractogram (bottom) at room temperature confirms that the simulated diffractogram from the single crystal structure is consistent with the experimental Compound 1, Pattern A diffractogram (FIG. 16). The differences observed between the patterns are highly likely due to the temperature employed during data collection for single crystal, which is 100 K, while in the latter case, the powder XRPD pattern is collected at ambient temperature (~295.15 K). Data collection at low temperatures could result in contraction of the unit cell, which therefore results in a shift in the 2θ peak position.

Example A-1: Parenteral Pharmaceutical Composition

To prepare a parenteral pharmaceutical composition suitable for administration by injection (subcutaneous, intravenous), 1-100 mg of Compound 1 disclosed herein, or a pharmaceutically acceptable solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of Compound 1 disclosed herein, or a pharmaceutically acceptable solvate thereof, is added to water (with optional solubilizer(s), optional buffer(s) and taste masking excipients) to provide a 20 mg/mL solution.

Example A-3: Oral Tablet

A tablet is prepared by mixing 20-50% by weight of Compound 1 disclosed herein, or a pharmaceutically acceptable solvate thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of Compound 1 disclosed herein, or a pharmaceutically acceptable solvate thereof, is optionally mixed with starch or other suitable powder blends. The mixture is incorporated into an oral dosage unit such as a hard gelatin capsule, which is suitable for oral administration.

In another embodiment, 10-500 mg of Compound 1 disclosed herein, or a pharmaceutically acceptable solvate thereof, is placed into Size 4 capsule, or size 1 capsule (hypromellose or hard gelatin) and the capsule is closed.

The examples and embodiments described herein are for illustrative purposes only and various modifications or changes suggested to persons skilled in the art are to be included within the spirit and purview of this application and scope of the appended claims.

What is claimed is:

1. A crystalline form of 4-[(3S)-3-aminopyrrolidin-1-yl]-6-cyano-5-(3,5-difluorophenyl)-N-[(2S)-1,1,1-trifluoropropan-2-yl]pyridine-3-carboxamide (Compound 1):
    wherein the crystalline form is crystalline Pattern A of Compound 1 characterized as having: an XRPD pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta as measured with Cu Kα1 radiation;
    wherein the crystalline form is crystalline Pattern B of Compound 1 characterized as having: an X-Ray Powder Diffraction (XRPD) pattern substantially the same as shown in FIG. 4 as measured with Cu Kα1 radiation;
    wherein the crystalline form is crystalline Pattern C of Compound 1 characterized as having an X-Ray Powder Diffraction (XRPD) pattern substantially the same as shown in FIG. 6 as measured with Cu Kα1 radiation; or
    wherein the crystalline form is crystalline Pattern D of Compound 1 characterized as having: an X-Ray Powder Diffraction (XRPD) pattern substantially the same as shown in FIG. 7 as measured with Cu Kα1 radiation.

2. The crystalline form of claim 1, wherein the crystalline form is crystalline Pattern A of Compound 1.

3. The crystalline form of claim 2, wherein the crystalline Pattern A of Compound 1 is characterized as having:
    an X-Ray Powder Diffraction (XRPD) pattern substantially the same as shown in FIG. 1 as measured with Cu Kα1 radiation;
    an XRPD pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta as measured with Cu Kα1 radiation;
    a Differential Scanning calorimetry (DSC) thermogram substantially the same as shown in: FIG. 2; or FIG. 3;
    a DSC thermogram with:
        an endotherm having onset at about 96.5° C. and peak at about 106.0° C.; or
        an endotherm having onset at about 86.6° C. and peak at about 101.4° C.;
    a Thermogravimetric Analysis (TGA) pattern substantially the same as shown in FIG. 3;
    a TGA pattern with a w/w loss of about 3.08% from 50 to 145° C.;
    reversible water uptake of about 0.7% between 2% and 95% relative humidity;
    an unchanged XRPD pattern after Dynamic Vapor Sorption (DVS) analysis between 2% and 95% relative humidity;
    an unchanged XRPD pattern after storage at 40° C./75% relative humidity for 7 days;
    an unchanged XRPD pattern after DSC analysis with thermal cycling from 30° C. to 118° C.;
    an XRPD pattern that converts to amorphous material after DSC analysis with thermal cycling from 30° C. to 150° C.;
    unit cell parameters substantially equal to the following at 100 K:

| Crystal System | Monoclinic |
|---|---|
| Space Group | P2$_1$ |
| a (Å) | 10.1810(2) |
| b (Å) | 9.9510(2) |
| c (Å) | 10.7342(2) |
| α | 90° |
| β | 114.6748(5)° |

| | |
|---|---|
| γ | 90° |
| V (Å³) | 988.20(3) |
| Z | 2 |
| Calculated Density (Mg/m³) | 1.537 |
| Absorption coefficient (mm⁻¹) | 1.169 |
| F(000) | 472 | or combinations thereof.

4. The crystalline form of claim 2, wherein the crystalline Pattern A of Compound 1 is characterized as having: an X-Ray Powder Diffraction (XRPD) pattern with peaks at 9.4±0.2° 2-Theta, 12.9±0.2° 2-Theta, 13.3±0.2° 2-Theta, 17.1±0.2° 2-Theta, 18.8±0.2° 2-Theta, 19.3±0.2° 2-Theta, and 20.7±0.2° 2-Theta as measured with Cu Kα1 radiation.

5. The crystalline form of claim 2, wherein the crystalline Pattern A of Compound 1 is characterized as having: an X-Ray Powder Diffraction (XRPD) pattern substantially the same as shown in FIG. 1 as measured with Cu Kα1 radiation.

6. The crystalline form of claim 5, wherein the crystalline Pattern A of Compound 1 is characterized as having: a Differential Scanning calorimetry (DSC) thermogram substantially the same as shown in FIG. 2.

7. The crystalline form of claim 4, wherein the crystalline Pattern A of Compound 1 is characterized as having: a Differential Scanning calorimetry (DSC) thermogram with an endotherm having onset at about 96.5° C. and peak at about 106.0° C.

8. The crystalline form of claim 4, wherein the crystalline Pattern A of Compound 1 is characterized as having: a Differential Scanning calorimetry (DSC) thermogram with an endotherm having onset at about 86.6° C. and peak at about 101.4° C.

9. The crystalline form of claim 5, wherein the crystalline Pattern A of Compound 1 is characterized as having: a Differential Scanning calorimetry (DSC) thermogram substantially the same as shown in FIG. 3.

10. The crystalline form of claim 4, wherein the crystalline Pattern A of Compound 1 is characterized as having: a Thermogravimetric Analysis (TGA) pattern with a w/w loss of about 3.08% from 50 to 145° C.

11. The crystalline form of claim 5, wherein the crystalline Pattern A of Compound 1 is characterized as having: a Thermogravimetric Analysis (TGA) pattern substantially the same as shown in FIG. 3.

12. The crystalline form of claim 4, wherein the crystalline Pattern A of Compound 1 is characterized as having: reversible water uptake of about 0.7% between 2% and 95% relative humidity.

13. The crystalline form of claim 4, wherein the crystalline Pattern A of Compound 1 is characterized as having:
an unchanged X-Ray Powder Diffraction (XRPD) pattern after Dynamic Vapor Sorption (DVS) analysis between 2% and 95% relative humidity;
an unchanged XRPD pattern after storage at 40° C./75% relative humidity for 7 days;
an unchanged XRPD pattern after Differential Scanning calorimetry (DSC) analysis with thermal cycling from 30° C. to 118° C.; or
an XRPD pattern that converts to amorphous material after DSC analysis with thermal cycling from 30° C. to 150° C.

14. The crystalline form of claim 2, wherein the crystalline Pattern A of Compound 1 is characterized as having unit cell parameters substantially equal to the following at 100 K:

| | |
|---|---|
| Crystal System | Monoclinic |
| Space Group | P2₁ |
| a (Å) | 10.1810(2) |
| b (Å) | 9.9510(2) |
| c (Å) | 10.7342(2) |
| α | 90° |
| β | 114.6748(5)° |
| γ | 90° |
| V (Å³) | 988.20(3) |
| Z | 2 |
| Calculated Density (Mg/m³) | 1.537 |
| Absorption coefficient (mm⁻¹) | 1.169 |
| F(000) | 472 |

15. The crystalline form of claim 2, wherein crystalline Pattern A of Compound 1 is a monohydrate.

16. The crystalline form of claim 2, wherein crystalline Pattern A of Compound 1 is substantially free of impurities.

17. The crystalline form of claim 2, wherein crystalline Pattern A of Compound 1 is substantially free of amorphous Compound A.

18. The crystalline form of claim 2, wherein crystalline Pattern A of Compound 1 is substantially free of other crystalline patterns of Compound A.

19. The crystalline form of claim 18, wherein crystalline Pattern A of Compound 1 is substantially free of crystalline Pattern B, crystalline Pattern C, and crystalline Pattern D of Compound 1.

20. The crystalline form of claim 2, wherein crystalline Pattern A of Compound 1 is at least about 90% pure.

21. The crystalline form of claim 2, wherein crystalline Pattern A of Compound 1 is at least about 95%, about 96%, about 97%, about 98%, or about 99% pure.

22. The crystalline form of claim 1, wherein the crystalline form is crystalline Pattern B of Compound 1.

23. The crystalline form of claim 22, wherein the crystalline Pattern B of Compound 1 is characterized as having:
an X-Ray Powder Diffraction (XRPD) pattern substantially the same as shown in FIG. 4 as measured with Cu Kα1 radiation;
a Differential Scanning calorimetry (DSC) thermogram substantially the same as shown in FIG. 5;
a DSC thermogram with five broad endothermic events having:
i. onset at about 46.4° C. and peak at about 75.4° C.;
ii. onset at about 160.0° C. and peak at about 177.1° C.;
iii. onset at about 191.4° C. and peak at about 198.3° C.;
iv. onset at about 238.6° C. and peak at about 256.2° C.; and
v. onset at about 259.1° C. and peak at about 292.0° C.;
or combinations thereof.

24. The crystalline form of claim 1, wherein the crystalline form is crystalline Pattern C of Compound 1.

25. The crystalline form of claim 24, wherein the crystalline Pattern C of Compound 1 is characterized as having an X-Ray Powder Diffraction (XRPD) pattern substantially the same as shown in FIG. 6 as measured with Cu Kα1 radiation.

26. The crystalline form of claim 1, wherein the crystalline form is crystalline Pattern D of Compound 1.

27. The crystalline pattern of claim 26, wherein the crystalline Pattern D of Compound 1 is characterized as having:

an X-Ray Powder Diffraction (XRPD) pattern substantially the same as shown in FIG. 7 as measured with Cu Kα1 radiation;

a Differential Scanning calorimetry (DSC) thermogram substantially the same as shown in FIG. 8;

a Differential Scanning calorimetry (DSC) thermogram with three broad endothermic events having:
  i. onset at about 47.4° C. and peak at about 72.2° C.;
  ii. onset at about 235.1° C. and peak at about 255.3° C.; and
  iii. onset at about 265.5° C. and peak at about 278.8° C.;

or combinations thereof.

28. A pharmaceutical composition comprising the crystalline form of claim 1 and at least one pharmaceutically acceptable excipient.

29. A method of treating hyperinsulinism in a mammal comprising administering the crystalline form of claim 1 to the mammal in need thereof.

* * * * *